(12) United States Patent
Vollmers et al.

(10) Patent No.: US 12,378,603 B2
(45) Date of Patent: Aug. 5, 2025

(54) NUCLEIC ACID SEQUENCING METHODS AND COMPUTER-READABLE MEDIA FOR PRACTICING SAME

(71) Applicant: The Regents of the University of California, Oakland, CA (US)

(72) Inventors: Christopher Vollmers, Santa Cruz, CA (US); Roger Volden, Santa Cruz, CA (US); Richard E. Green, Santa Cruz, CA (US); Theron Palmer, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/048,420

(22) PCT Filed: Apr. 19, 2019

(86) PCT No.: PCT/US2019/028312
§ 371 (c)(1),
(2) Date: Oct. 16, 2020

(87) PCT Pub. No.: WO2019/204720
PCT Pub. Date: Oct. 24, 2019

(65) Prior Publication Data
US 2021/0079461 A1    Mar. 18, 2021

Related U.S. Application Data

(60) Provisional application No. 62/660,714, filed on Apr. 20, 2018.

(51) Int. Cl.
*C12P 19/34* (2006.01)
*C12Q 1/6869* (2018.01)

(52) U.S. Cl.
CPC ..... *C12Q 1/6869* (2013.01); *C12Q 2525/307* (2013.01); *C12Q 2531/125* (2013.01);
(Continued)

(58) Field of Classification Search
USPC ....... 435/6.1, 6.11, 6.12, 91.1, 91.2; 436/94, 436/501; 536/23.1, 24.3, 24.33, 25.3
See application file for complete search history.

(56) References Cited

U.S. PATENT DOCUMENTS 9,481,908 B2   11/2016   Olasagasti et al.
2004/0219565 A1* 11/2004   Kauppinen ............ C07H 19/16
                                                                 435/5
(Continued)

FOREIGN PATENT DOCUMENTS

WO    2016077313    5/2016

OTHER PUBLICATIONS

Kent, BLAT-The BLAST-Like Alignment Tool. Genome Research, 12, 656-664, 2002.*
(Continued)

*Primary Examiner* — Frank W Lu
(74) *Attorney, Agent, or Firm* — Brian E. Davy; Bozicevic, Field & Francis LLP

(57) ABSTRACT

Provided are methods of nucleic acid sequencing. The methods include producing a circularized DNA including a full-length cDNA and a known heterologous sequence, and performing rolling circle amplification using the circularized DNA as template to produce a concatemer including repeating segments including the full-length cDNA and the known heterologous sequence. The methods further include obtaining a raw sequencing read of the concatemer using a nanopore, identifying the repeating segments in the raw sequencing read, and producing a consensus sequence of the full-length cDNA based on the sequences of the repeating
(Continued)

segments. Computer-readable media, computing devices, and systems that find use, e.g., in practicing the methods of the present disclosure are also provided.

10 Claims, 12 Drawing Sheets

Specification includes a Sequence Listing.

(52) U.S. Cl.
CPC .  *C12Q 2537/165* (2013.01); *C12Q 2563/179* (2013.01); *C12Q 2565/631* (2013.01)

(56) References Cited

U.S. PATENT DOCUMENTS

| | | | |
|---|---|---|---|
| 2006/0166245 A1* | 7/2006 | Potter | C12Q 1/686 |
| | | | 435/6.12 |
| 2011/0269631 A1* | 11/2011 | Fu | C12Q 1/6858 |
| | | | 506/7 |
| 2014/0051068 A1 | 2/2014 | Cherf et al. | |
| 2014/0255931 A1 | 9/2014 | Porreca et al. | |
| 2015/0057948 A1 | 2/2015 | Reid et al. | |
| 2015/0346149 A1 | 12/2015 | Brown et al. | |
| 2016/0376647 A1 | 12/2016 | Travers et al. | |
| 2017/0044606 A1 | 2/2017 | Lo et al. | |
| 2018/0282800 A1* | 10/2018 | Li | C12Q 1/6869 |

OTHER PUBLICATIONS

Szajda et al., Toward A Practical Data Privacy Scheme for A Distributed Implementation of the Smith-Waterman Genome Sequence Comparison Algorithm. NDSS Symposium, pp. 1-13, Feb. 2006).*
"Smith-Waterman algorithm" from Wikipedia. Printed on Jan. 14, 2022.*
Lee et al., Multiple sequence alignment using partial order graphs. Bioinformatics, 18, 452-464, 2002.*
Vaser et al., Racon—Rapid consensus module for raw de novo genome assembly of long uncorrected readsOxford Nanopore Technologies London Calling 2016.*
Salimullah et al., NanoCAGE: A High-Resolution Technique to Discover and Interrogate Cell Transcriptomes. Cold Spring Harb Protoc., pp. 96-110, 2011.*
"Gibson assembly" from NEB. Printed on Mar. 23, 2024.*
Feng et al. (2015) "Nanopore-based Fourth-generation DNA Sequencing Technology" Genomics, Proteomics & Bioinformatics, 13(1):4-16.
Lieberman et al. (2010) "Processive Replication of Single DNA Molecules in a Nanopore Catalyzed by phi29 DNA Polymerase" J. Am. Chem. Soc., 132(50):17961-17972.
Stoddart et al. (2009) "Single-nucleotide discrimination in immobilized DNA oligonucleotides with a biological hanopore" PNAS, 106(19):7702-7.
NEBuilder® HiFi DNA Assembly Master Mix/ NEBuilder HiFi DNA Assembly Cloning Kit, New England BioLabs Inc., NEB #E2621S/L/X, #E5520S, (2023) 15 pages.

* cited by examiner

```
FMC63 epitope

>CD19_Protein
90 -QMGGFYLCQPGPPPSEKAWQPGWTVNVEGSGELFRWNVSDLGGLGCGLKNRSSEGPSSPSGKLMSPKLYVWAKDRPEIWEGEPPCLPPRDSLNQSLSQDLTMAPGST
   LMLSCGVPPDSVSRGPLSWTHVHPKGPKSLLSLELKDDRPARDMWVMETGLLLPRATAQDAGKYYCHRGNLTMSFHLEI-276

>A16_TS03
90 -QMGGFYLCQPGPPPSEKAWQPGWTVNVEGSGEGRAGAGAGGEKGGHHGQKRSAATMetELERGAGGIEGETRS-------------------------------
   -----------------------------------------------------------------------------------

>A16_TS04
                                                                        -MSPKLYVWAKDRPEIWEGEPPCLPPRDSLNQSLSQDLTMAPGST
   LMLSCGVPPDSVSRGPLSWTHVHPKGPKSLLSLELKDDRPARDMWVMETGLLLPRATAQDAGKYYCHRGNLTMSFHLEI-125

>A13_TS04
90 -QMGGFYLCQPGPPPSEKAWQPGWTVNVEGSGEGRAGAGAGGEKGGHHGQKRSAATMetELERGAGGIEGETRS-------------------------------
   -----------------------------------------------------------------------------------

>A9_TS03
                                                                        MWVMETGLLLPRATAQDAGKYYCHRGNLTMSFHLEI-38
```

NUCLEIC ACID SEQUENCING METHODS AND COMPUTER-READABLE MEDIA FOR PRACTICING SAME

CROSS-REFERENCE TO RELATED APPLICATIONS

This application claims the benefit of U.S. Provisional Patent Application No. 62/660,714, filed Apr. 20, 2018, which application is incorporated herein by reference in its entirety.

INTRODUCTION

Short-read RNAseq has been used for the analysis of transcriptomes for over a decade (1). The massive read output of Illumina sequencers makes it possible to quantify gene expression accurately using this approach. However, to accommodate Illumina sequencers' short read-length, RNA or cDNA has to be fragmented during sample preparation, thereby losing long distance RNA transcript isoform information. Specialized protocols like SLR (2) or spISO-seq (3) have been used successfully to recover long-distance information but they require either specialized instrumentation or complex workflows. The SLR method assembles mostly incomplete cDNA molecules, and has limited throughput, while spISO-seq requires a 10× Genomics instrument and generates read clouds which capture long distance information, and yet cannot assemble full-length cDNA molecules.

In contrast, long-read sequencing technology has the capability to sequence entire cDNA molecules end-to-end. The Pacific Biosciences ("PacBio") Iso-Seq pipeline for cDNA sequencing (4) has been used to investigate a wide range of transcriptomes (5, 6). The PacBio Sequel sequencer produces ~200 k accurate circular consensus reads of full-length cDNA molecules per run.

Nanopore sequencing technology (e.g., provided by Oxford Nanopore Technologies, or "ONT") could present a valuable alternative for cDNA sequencing, because the ONT MinION can currently generate more than one million reads per run. The ONT MinION can sequence cDNA at high throughput, but the data analysis is challenging (7, 8) due to a substantial error rate. Base level identification of splice junction sequence is one challenge.

One strategy to increase the base accuracy of cDNA sequences produced by the higher-output ONT MinION sequencer is to apply the circular consensus principle applied by PacBio sequencers. By sequencing 16S amplicon molecules, the INC-seq (9) method has shown that this is possible, in principle. However, the reported throughput of a few thousand reads per-run would be insufficient for transcriptome analysis. Further, like PacBio technology, the INC-Seq method uses blunt-end ligation to circularize double-stranded DNA molecules, which does not differentiate between full-length or fragmented DNA molecules. In summary, current technology produces reads that are either inaccurate (ONT), potentially incomplete (Illumina, PacBio, ONT, INC-seq), or too low-throughput/expensive (PacBio, SLR, INC-seq) to enable high-throughput complete cDNA sequencing.

SUMMARY

Provided are methods of nucleic acid sequencing. The methods include producing a circularized DNA including a full-length cDNA and a known heterologous sequence, and performing rolling circle amplification using the circularized DNA as template to produce a concatemer including repeating segments including the full-length cDNA and the known heterologous sequence. The methods further include obtaining a raw sequencing read of the concatemer using a nanopore, identifying the repeating segments in the raw sequencing read, and producing a consensus sequence of the full-length cDNA based on the sequences of the repeating segments. Computer-readable media, computing devices, systems and kits that find use, e.g., in practicing the methods of the present disclosure are also provided.

R2C2 consensus reads per cell is shown of the indicated human gene loci. Data R2C2 consensus reads from different cell are separated by black lines. Transcript and read direction are shown by colors (Blue: +strand, Yellow: −strand). Red lines indicated TSSs identified based on the same cDNA using Tn5Prime-based Illumina sequencing.

Figure 6:
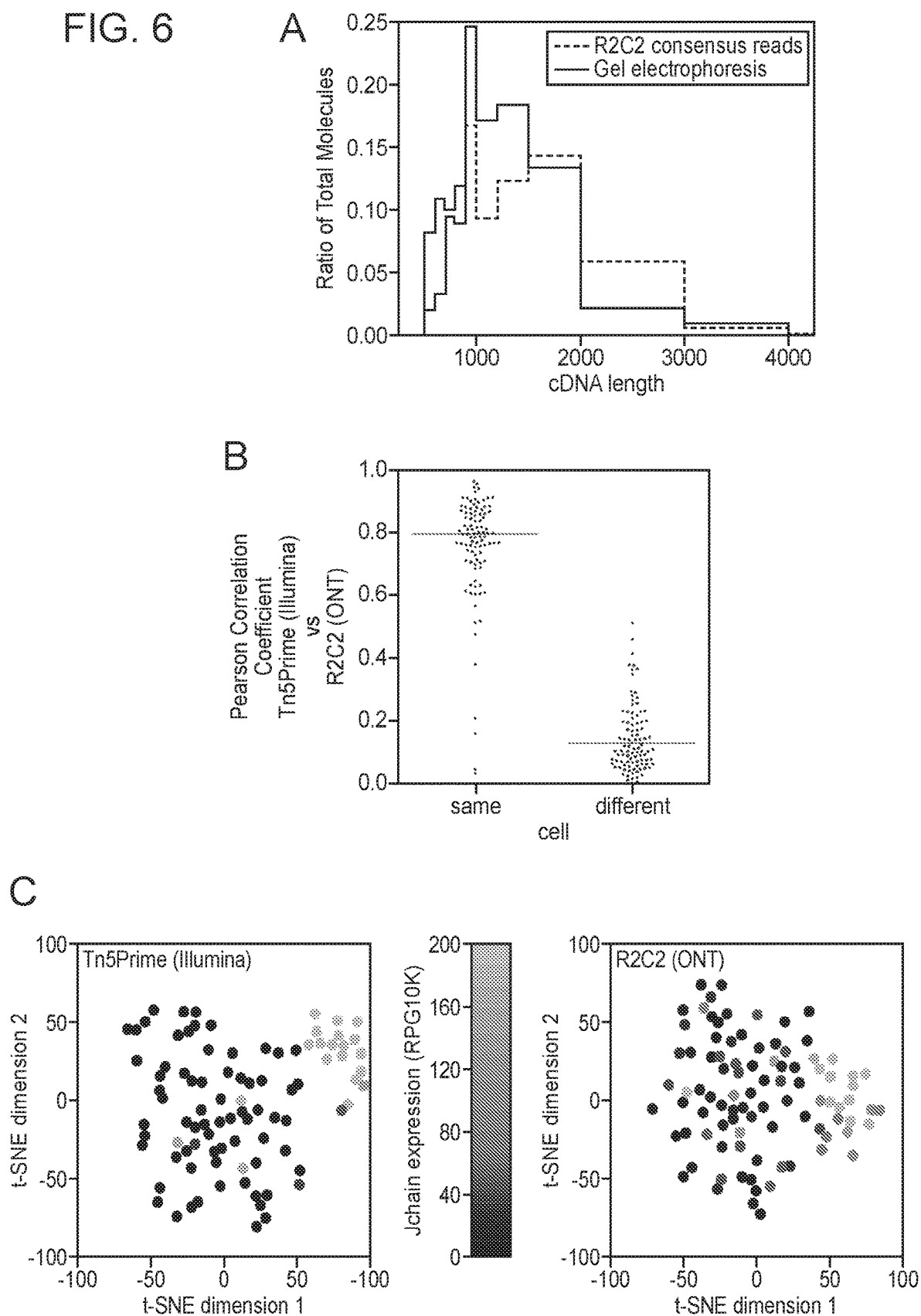

FIG. 6 Length bias and gene expression quantification. Panel A: B cell cDNA molecule length distribution as determined by electrophoresis on 2% agarose gel is compared to R2C2 consensus read length distribution. Panel B: Pearson correlation coefficient (r) is shown for R2C2 and Illumina based gene expression quantification of the same of different cells. Red lines indicate medians. All 96 correlation coefficient from same cell comparisons and 96 subsampled correlation coefficients from different cell comparisons are shown as a swarmplot to display their distributions. Panel C: t-SNE dimensional reduction plots of the same 96 B cells whose transcriptome were quantified with either the Tn5Prime Illumina based method or the R2C2 ONT based method. Cells are colored based on the Jchain expression which is strongly associated with plasmablast cell identity.

FIG. 7A-7C Identification of isoforms in B cell surface receptor genes. Genome browser views of Transcriptome annotation, isoforms identified by Mandalorion, and R2C2 consensus reads ([Panel C]] 7C only, down-sampled to 20 reads) are shown for the indicated gene loci. Transcript and read direction is shown by colors (Blue: +strand, Yellow:-strand). Cell IDs are indicated by combinations of A and TSO indexes.

FIG. 8 Predicted amino acid sequences of CD19 isoforms lack FMC63 CAR-T cell epitope CD19 isoforms identified by Mandalorion based on single cell R2C2 consensus reads were manually aligned to the CD19 protein reference (on top). Red letters indicate mismatches to the CD19 protein reference. The FMC63 epitope is shown in green. The amino acid sequences in the alignment from Top to Bottom: SEQ ID NOs:14-18.

DETAILED DESCRIPTION

Provided are methods of nucleic acid sequencing. The methods include producing a circularized DNA including a full-length cDNA and a known heterologous sequence, and performing rolling circle amplification using the circularized DNA as template to produce a concatemer including repeating segments including the full-length cDNA and the known heterologous sequence. The methods further include obtaining a raw sequencing read of the concatemer using a nanopore, identifying the repeating segments in the raw sequencing read, and producing a consensus sequence of the full-length cDNA based on the sequences of the repeating segments. Computer-readable media, computing devices, systems and kits that find use, e.g., in practicing the methods of the present disclosure are also provided.

Before the methods, computer-readable media, computing devices, and systems of the present disclosure are described in greater detail, it is to be understood that the methods, computer-readable media, computing devices, and systems are not limited to particular embodiments described, as such may, of course, vary. It is also to be understood that the terminology used herein is for the purpose of describing particular embodiments only, and is not intended to be limiting, since the scope of the methods, computer-readable media, computing devices, and systems will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, computer-readable media, computing devices, and systems. The upper and lower limits of these smaller ranges may independently be included in the smaller ranges and are also encompassed within the methods, computer-readable media, computing devices, and systems, subject to any specifically excluded limit in the stated range. Where the stated range includes one or both of the limits, ranges excluding either or both of those included limits are also included in the methods, computer-readable media, computing devices, and systems.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, computer-readable media, computing devices, and systems belong. Although any methods, computer-readable media, computing devices, and systems similar or equivalent to those described herein can also be used in the practice or testing of the methods, computer-readable media, computing devices, and systems, representative illustrative methods, computer-readable media, computing devices, and systems are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, computer-readable media, computing devices, and systems are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, computer-readable media, computing devices, and systems, which are, for clarity, described in the context of separate embodiments, may also be provided in combination in a single embodiment. Conversely, various features of the methods, computer-readable media, computing devices, and systems, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, computer-readable media, computing devices, and systems and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of nucleic acid sequencing. The methods include producing a circularized DNA including a full-length cDNA and a known heterologous sequence, and performing rolling circle amplification using the circularized DNA as template to produce a concatemer including repeating segments including the full-length cDNA and the known heterologous sequence. The methods further include obtaining a raw sequencing read of the concatemer using a nanopore, identifying the repeating segments in the raw sequencing read, and producing a consensus sequence of the full-length cDNA based on the sequences of the repeating segments.

As noted above, there are issues with both Pacific Biosciences (PacBio) and current nanopore-based long-read sequencing technologies that prevent their widespread adoption. Briefly, PacBio sequencers produce low numbers of reads with high accuracy, while nanopore-based sequencers produce higher numbers of reads with lower accuracy. Here we introduce and validate a new long-read nanopore-based sequencing method. At the same cost, the methods of the present disclosure (sometimes referred to herein as the Rolling Circle Amplification to Contameric Consensus (R2C2) method) generate, e.g., more accurate reads of full-length RNA transcript isoforms than any other available long-read sequencing method. These reads can then be used to generate, e.g., isoform-level transcriptomes for both genome annotation and differential expression analysis in bulk or single cell samples. Aspects of the methods will now be described in detail.

The subject methods include producing a circularized DNA, the circularized DNA including a full-length complementary DNA (cDNA) and a known heterologous sequence. In the context of messenger RNA, a "full-length" cDNA is a cDNA that includes at least the complement of the entire coding portion of the mRNA from which the cDNA is produced/derived. The cDNA may be the initial cDNA molecule produced upon reverse transcription of the mRNA, or the cDNA may be a copy of such initial molecule, e.g., an amplicon of such initial molecule.

Full-length cDNAs may be produced by performing a reverse transcription reaction on an RNA sample of interest. The RNA sample of interest may be isolated from a single cell, a plurality of cells (e.g., cultured cells), a tissue, an organ, or an organism (e.g., bacteria, yeast, or the like). In certain aspects, the RNA sample of interest is isolated from a cell(s), tissue, organ, and/or the like of an animal. In some embodiments, the animal is a mammal (e.g., a mammal from the genus Homo, a rodent (e.g., a mouse or rat), a dog, a cat, a horse, a cow, or any other mammal of interest). In other aspects, the nucleic acid sample is isolated/obtained from a source other than a mammal, such as bacteria, yeast, insects (e.g., *Drosophila*), amphibians (e.g., frogs (e.g., *Xenopus*)), viruses, plants, or any other non-mammalian nucleic acid sample source.

Approaches, reagents and kits for isolating RNA from sources of interest are known in the art and commercially available. For example, kits for isolating RNA from a source of interest include the RNeasy®, QIAamp®, QIAprep® and QIAquick® nucleic acid isolation/purification kits by Qiagen, Inc. (Germantown, Md.); the ChargeSwitch®, Purelink®, GeneCatcher® nucleic acid isolation/purification kits by Life Technologies, Inc. (Carlsbad, CA); the NucleoMag®, NucleoSpin®, and NucleoBond® nucleic acid isolation/purification kits by Clontech Laboratories, Inc. (Mountain View, CA), and TRIzol™ reagent by Invitrogen™. In certain aspects, the RNA is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, CA), and the NucleoSpin® FFPE kits by Clontech Laboratories, Inc. (Mountain View, CA).

The RNA from which the cDNA is produced may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, or a ribozyme.

Reverse transcription may be accomplished using a suitable primer (e.g., an oligo dT or other suitable primer) and a suitable polymerase (e.g., reverse transcriptase) to carry out a first-strand cDNA synthesis reaction. Reagents and kits for carrying out such reverse transcription are readily available and include, e.g., the SMART® cDNA Library Construction Kit or the In-Fusion® SMARTer® Directional cDNA Library Construction Kit available from Clontech Laboratories, Inc. (Mountain View, CA); and the SuperScript IV First-Strand Synthesis System available from ThermoFisher Scientific.

In some embodiments, reverse transcription is carried out using an oligo(dT) primer having a 5' non-hybridizing region that includes a sequence heterologous to the RNA. Such embodiments may further include a polymerase extension reaction to produce the cDNA, where upon reaching the 5' end of the RNA template, a terminal transferase activity of the polymerase (e.g., MMLV reverse transcriptase) adds a few additional nucleotides (e.g., deoxycytidine) to the 3' end of the newly synthesized cDNA strand. These bases may then function as a template switch (TS) oligonucleotide-anchoring site. Upon base pairing between the TS oligo and the appended additional nucleotides (e.g., deoxycytidine stretch), the reverse transcriptase "switches" template strands, from the template RNA to the TS oligo, and continues replication to the 5' end of the TS oligo. By doing so, the resulting cDNA contains the complete 5' end of the transcript, and one or more heterologous sequences (e.g., index sequence, or the like) may be added to one or both ends of the reverse transcription product. Along with tagging of the cDNA 3' end by oligo dT primers, this approach makes it possible to efficiently amplify the entire full-length transcript pool in a completely sequence-independent manner.

As used herein, a "heterologous" sequence is a nucleic acid sequence not found within or immediately adjacent to the RNA or cDNA in nature. By "known" heterologous sequence is meant the practitioner of the subject methods knows that the heterologous sequence is being added to the RNA and/or cDNA (e.g., during reverse transcription and/or cDNA amplification) prior to or during circularization. The known heterologous sequence may be a sequence such as an index sequence. In certain aspects, the known heterologous sequence is a sequencing adapter or portion thereof. By "sequencing adapter" is meant a nucleic acid domain selected from: a domain (e.g., a "capture site" or "capture sequence") that specifically binds to a surface-attached sequencing platform oligonucleotide; a sequencing enzyme-binding domain (e.g., a nucleic acid domain that binds an enzyme (e.g., a helicase) employed in a nanopore-based sequencing system; a sequencing primer binding domain; a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); an index sequence (e.g., a molecular index tag, such as a randomized tag of 4, 6, or other number of nucleotides); a complement of any such domains; or any combination thereof. In some embodiments, the known heterologous sequence is a combination of heterologous sequences.

In certain aspects, the methods include PCR amplifying the full-length cDNA prior to circularization. In some embodiments, amplification of the full-length cDNA is facilitated by the presence of at least one known heterologous sequence present at one or both ends of the full-length cDNA. For example, the amplification may be carried out using a PCR primer pair in which one primer hybridizes to a known heterologous sequence (e.g., an index sequence) at one end of the full-length cDNA and the other primer hybridizes to a known heterologous sequence (e.g., an index sequence) at the opposite end of the full-length cDNA. The resulting amplicons will include the full-length cDNA and a known heterologous sequence or portion thereof at each end.

Circularizing a nucleic acid that includes the full-length cDNA and a known heterologous sequence may be performed using any suitable approach. In one example, the two ends of such a molecule are ligated to each other using a suitable ligase, e.g., a ligase suitable for blunt end ligation or sticky end ligation. Blunt end ligation could be employed by providing a heterologous sequence having a blunt end at one end of the full-length cDNA and a heterologous sequence having a blunt end at the other end of the full-length cDNA. Sticky end ligation could be employed by providing a heterologous sequence having a sticky end at one end of the full-length cDNA and a heterologous sequence having a complementary sticky end at the other end of the full-length cDNA.

Figure 1:
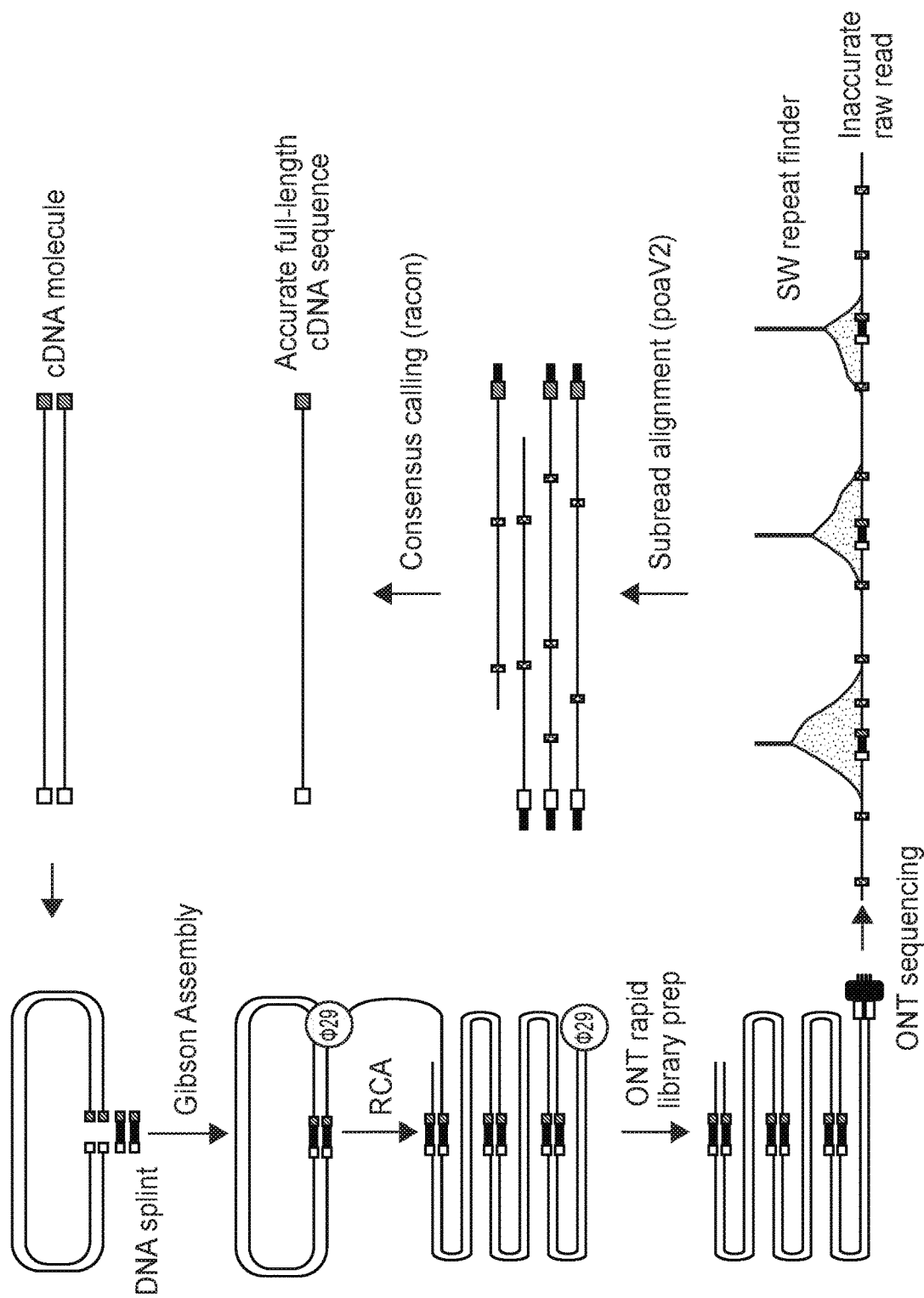
FIG. 1 Overview of a method according to one embodiment of the present disclosure. cDNA is circularized using Gibson Assembly, amplified using RCA, and sequenced using the ONT MinION. The resulting raw reads are split into subreads containing full-length or partial cDNA sequences, which are combined into an accurate consensus sequences using a workflow of the present disclosure (Concatemeric Consensus Caller using POA, or "C3POa") which relies on a custom algorithm to detect DNA splints as well as poaV2 and racon.

In other aspects, the circularized DNA is produced from a cDNA including a first heterologous sequence at a first end and a second heterologous sequence at the end opposite the first end; circularization is achieved using a splint oligonucleotide including sequences complementary to the first and second heterologous sequences; and the known heterologous sequence of the circularized DNA includes the first and second heterologous sequences or portions thereof. In such aspects, a Gibson assembly approach or modified version thereof (e.g., NEBuilder Hifi DNA assembly) could be used to join the ends of the nucleic acid using the splint oligonucleotide. An example of such an approach is schematically illustrated in FIG. 1 and described in detail in the Experimental section below.

Once the circularized DNA is produced, the methods further include performing rolling circle amplification using the circularized DNA as template to produce a concatemer including repeating segments including the full-length cDNA and the known heterologous sequence. As used herein, the term "rolling circle amplification" or "RCA" refers to an amplification (e.g., isothermal amplification) that generates linear concatemerized copies of a circular nucleic acid template using a strand-displacing polymerase. During RCA, the polymerase continuously adds single nucleotides to a primer (e.g., an oligonucleotide primer or a primer produced by nicking a double-stranded circular DNA (e.g., using an endonuclease) annealed to the circular template which results in a concatemer single-stranded (ssDNA) that contains tandem repeats (e.g., tens, hundreds or more tandem repeats) complementary to the circular template. In some embodiments, a primer that hybridizes to the known heterologous sequence or portion thereof is employed. In other aspects, a random primer (e.g., a random hexamer) is employed. Suitable strand-displacing polymerases that may be employed include, but are not limited to, Phi29 polymerase, Bst polymerase, and Vent exo-DNA polymerase. Reagents, protocols and kits for performing RCA are known and include, e.g., the RCA DNA Amplification Kit available from Molecular Cloning Laboratories; and TruePrime RCA Kit available from Expedeon.

As summarized above, the methods of the present disclosure further include obtaining a raw sequencing read of the concatemer using a nanopore. In certain aspects, obtaining a raw sequencing read of the concatemer using a nanopore includes applying a potential difference across the nanopore, and detecting (e.g., monitoring) electrical signals from the nanopore while exposing the concatemer to the nanopore in a sequential manner. In some embodiments, exposing the concatemer to the nanopore in a sequential manner includes translocating at least a portion of the concatemer through the nanopore.

Any device/apparatus suitable for exposing the concatemer to a nanopore (e.g., translocating the concatemer through a nanopore) and detecting/monitoring ionic current through the nanopore during the exposing/translocating may be employed when practicing the subject methods. For example, a suitable device may include a chamber including an aqueous solution and a membrane that separates the chamber into two sections, the membrane including a nanopore formed therein. Electrical measurements may be made using single channel recording equipment such as that described, e.g., in Lieberman et al. (2010) *J. Am. Chem. Soc.* 132(50):17961-72; Stoddart et al. (2009) *PNAS* 106(19): 7702-7; U.S. Pat. No. 9,481,908; and U.S. Patent Application Publication No. US2014/0051068; the disclosures of which are incorporated herein by reference in their entireties for all purposes. Alternatively, electrical measurements may be made using a multi-channel system, for example as described in U.S. Patent Application Publication No. US2015346149, the disclosure of which is incorporated herein by reference in its entirety for all purposes.

In nanopore sequencing, the nanopore serves as a biosensor and provides the sole passage through which an ionic solution on the cis side of the membrane contacts the ionic solution on the trans side. A constant voltage bias (trans side positive) produces an ionic current through the nanopore and drives ssDNA or ssRNA in the cis chamber through the pore to the trans chamber. A processive enzyme (e.g., a helicase, polymerase, nuclease, or the like) may be bound to the polynucleotide such that its step-wise movement controls and ratchets the nucleotides through the small-diameter nanopore, nucleobase by nucleobase. Because the ionic conductivity through the nanopore is sensitive to the presence of the nucleobase's mass and its associated electrical field, the ionic current levels through the nanopore reveal the sequence of nucleobases in the translocating strand. A patch clamp, a voltage clamp, or the like, may be employed.

Suitable conditions for measuring ionic currents through transmembrane pores (e.g., protein pores, solid state pores, etc.) are known in the art. Typically, a voltage is applied across the membrane and pore. The voltage used may be from +2 V to −2 V, e.g., from −400 mV to +400 mV. The voltage used may be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage may be in the range of from 100 mV to 240 mV, e.g., from 120 mV to 220 mV.

The methods are typically carried out in the presence of a suitable charge carrier, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or I-ethyl-3-methyl imidazolium chloride. Generally, the salt is present in the aqueous solution in the chamber. Potassium chloride (KCl), sodium chloride (NaCl) or cesium chloride (CsCl) may be used, for example. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M, or from 1 M to 1.4 M. The salt concentration may be from 150 mM to 1 M. The methods are preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

In some embodiments, the rate at which the concatemer is exposed to the nanopore is controlled using a processive enzyme. Non-limiting examples of processive enzymes that may be employed include polymerases (e.g., a phi29 or other suitable polymerase) and helicases, e.g., a He1308 helicase, a RecD helicase, a Tral helicase, a Tral subgroup helicase, an XPD helicase, or the like. The concatemer may be bound by the processive enzyme (e.g., by binding of the processive enzyme to a recognition site present in a sequencing adapter located at an end of the concatemer), followed by the resulting complex being drawn to the nanopore, e.g., by a potential difference applied across the nanopore. In other aspects, the processive enzyme may be located at the nanopore (e.g., attached to or adjacent to the nanopore) such that the processive enzyme binds the concatemer upon arrival of the concatemer at the nanopore.

The nanopore may be present in a solid-state film, a biological membrane, or the like. In some embodiments, the nanopore is a solid-state nanopore. In other embodiments, the nanopore is a biological nanopore. The biological nanopore may be, e.g., an alpha-hemolysin-based nanopore, a *Mycobacterium smegmatis* porin A (MspA)-based nanopore, or the like.

Details for obtaining raw sequencing reads of nucleic acid molecules of interest using nanopores are described, e.g., in Feng et al. (2015) *Genomics, Proteomics & Bioinformatics* 13(1):4-16. Raw sequencing reads may be obtained using, e.g., a MinION™, GridIONx5™, PromethION™, or SmidgION™ nanopore-based sequencing system, available from Oxford Nanopore Technologies. Detailed design considerations and protocols for carrying out nanopore-based sequencing are provided with such systems.

Once a raw sequencing read of the concatemer is obtained, the present methods further include identifying the repeating segments in the raw sequencing read. In some embodiments, identifying the repeating segments in the raw sequencing read includes identifying at least one sequence of the known heterologous sequence in the raw sequencing read. In certain aspects, the at least one sequence of the known heterologous sequence is identified in the raw sequencing read using a BLAST-Like Alignment Tool (BLAT).

In some embodiments, identifying the repeating segments in the raw sequencing read includes subjecting the raw sequencing read to a modified Smith-Waterman self-to-self alignment. The Smith-Waterman algorithm is a dynamic programming algorithm that performs local sequence alignment for determining similar regions between two strings of nucleic acid or protein sequences. Instead of looking at the entire sequence, the Smith-Waterman algorithm compares segments of all possible lengths and optimizes the similarity measure. In certain aspects, identifying the repeating segments in the raw sequencing read comprises parsing a score matrix of the modified Smith-Waterman self-to-self alignment.

In certain aspects, producing a consensus sequence of the full-length cDNA includes combining the sequences of the repeating segments using a partial order alignment (POA).

Once a consensus sequence of the full-length cDNA is produced, the methods of the present disclosure may further include subjecting the consensus sequence to error-correction. In some embodiments, subjecting the consensus sequence to error-correction comprises subjecting the consensus sequence to rapid consensus (Racon).

Detailed guidance and example approaches for obtaining a raw sequencing read of a concatemer using a nanopore, identifying repeating segments in the raw sequencing read, producing a consensus sequence of the full-length cDNA based on the sequences of the repeating segments, performing any desired error correction, etc. may be found in the Experimental section below.

As demonstrated in the Experimental section below, the present methods enable the production of a large number of full-length cDNA consensus sequences in a single sequencing run. In some embodiments, 100,000 or greater, 150,000 or greater, 200,000 or greater, 250,000 or greater, 300,000 or greater, 350,000 or greater, 400,000 or greater, 450,000 or greater, or 500,000 or greater full-length cDNA consensus sequences are produced in a single sequencing run. Also as demonstrated in the Experimental section below, the full-length cDNA consensus sequences exhibit high median base accuracy. In certain aspects, the median base accuracy is 80% or greater, 85% or greater, 90% or greater, 95% or greater, or 99% or greater.

In some embodiments, the methods of the present disclosure further include producing an isoform-level transcriptome for a bulk sample (e.g., an RNA sample obtained from two or more cells) or a single cell sample based on the full-length cDNA consensus sequences produced by the methods.

Computer-Readable Media, Computer Devices and Systems

As summarized above, the present disclosure also provides non-transitory computer readable media. Such media include instructions that cause a computing device to produce a consensus full-length cDNA sequence from a raw nanopore sequencing read of a concatemer comprising repeating segments comprising a full-length cDNA and a known heterologous sequence. When executed by the computing device, the instructions cause the computing device to identify the repeating segments in the raw sequencing read, and produce a consensus sequence of the full-length cDNA based on sequences of the repeating segments.

In some embodiments, to identify the repeating segments in the raw sequencing read, the instructions cause the computing device to identify at least one sequence of the known heterologous sequence in the raw sequencing read. In certain aspects, to identify the repeating segments in the raw sequencing read, the raw sequencing read is subjected to a modified Smith-Waterman self-to-self alignment. For example, the instructions may cause the computing device to parse a score matrix of the modified Smith-Waterman self-to-self alignment. In certain aspects, the instructions cause the computing device to produce a consensus sequence of the full-length cDNA by combining the sequences of the repeating segments using a partial order alignment (POA). In some embodiments, the instructions further cause the computing device to subject the consensus sequence to error-correction, e.g., using rapid consensus (Racon).

Instructions can be coded onto a non-transitory computer-readable medium in the form of "programming", where the term "computer-readable medium" as used herein refers to any non-transitory storage or transmission medium that participates in providing instructions and/or data to a computer for execution and/or processing. Examples of storage media include a hard disk, optical disk, magneto-optical disk, CD-ROM, CD-R, magnetic tape, non-volatile memory card, ROM, DVD-ROM, Blue-ray disk, solid state disk, network attached storage (NAS), etc., whether or not such devices are internal or external to the computer. A file containing information can be "stored" on computer readable medium, where "storing" means recording information such that it is accessible and retrievable at a later date by a computer.

The instructions may be in the form of programming that is written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as many others.

Also provided by the present disclosure are computer devices. The computer devices include a processor and any of the non-transitory computer-readable media of the present disclosure. The computing device may be part of a system that includes a nanopore sequencing device.

The following examples are offered by way of illustration and not by way of limitation.

EXPERIMENTAL

Introduction

High-throughput short-read sequencing has revolutionized how transcriptomes are quantified and annotated. However, while Illumina short-read sequencers can be used to analyze entire transcriptomes down to the level of individual splicing events with great accuracy, they fall short of analyzing how these individual events are combined into complete RNA transcript isoforms. Because of this shortfall, long-read sequencing is required to complement short-read sequencing to analyze transcriptomes on the level of full-length RNA transcript isoforms. However, there are issues with both Pacific Biosciences (PacBio) and Oxford Nanopore Technologies (ONT) long-read sequencing technologies that prevent their widespread adoption. Briefly, PacBio sequencers produce low numbers of reads with high accuracy, while ONT sequencers produce higher numbers of reads with lower accuracy. Introduced and validated herein is a new long-read nanopore-based sequencing method. At the same cost, the sequencing method reported herein (sometimes referred to herein as Rolling Circle Amplification to Concatemeric Consensus (R2C2) method) generates more accurate reads of full-length RNA transcript isoforms than any other available long-read sequencing method. These reads can then be used to generate isoform-level transcriptomes for both genome annotation and differential expression analysis in bulk or single cell samples.

Subtle changes in RNA transcript isoform expression can have dramatic effects on cellular behaviors in both health and disease. As such, comprehensive and quantitative analysis of isoform-level transcriptomes would open an entirely new window into cellular diversity in fields ranging from developmental to cancer biology. The present method is the first method with sufficient throughput and accuracy to make the comprehensive and quantitative analysis of RNA transcript isoforms in bulk and single cell samples economically feasible.

First, the present method was benchmarked against PacBio Iso-Seq for the analysis of the same synthetic transcript mixture. Second, the present method was applied to analyze the transcriptomes of 96 single B cells derived from a healthy adult. Demonstrated herein is that the present method, in a single run, can generate over 400,000 reads covering full-length cDNA molecules with a median base accuracy of 94%. Using a new version of the inventors' Mandalorion pipeline, these reads can be used to identify high confidence RNA transcript isoforms present in bulk or single cell transcriptomes. Illustrating the power of this approach, it was found that many of the B cells in the present study express RNA transcript isoforms of the CD19 gene that lack the epitope targeted by CAR T-cell therapy (10-12).

Example 1—Improvement of the Base Accuracy of the ONT MinION

To benchmark the R2C2 method, SIRV E2 synthetic spike-in RNA was analyzed. First, the synthetic spike-in RNA was reverse transcribed and amplified using the Tn5Prime (13) protocol, which is a modification of the Smart-seq2 protocol which uses a distinct template switch oligo containing 7 nucleotide sample indexes during reverse transcription. Amplification introduces an additional 8 nucleotide index into the cDNA molecules. The amplified cDNA was then circularized using a DNA splint and the NEBuilder Hifi DNA Assembly Master Mix, a proprietary variant of Gibson Assembly. The DNA splint was designed to circularize only full-length cDNA terminating on both ends in sequences complementary to the primers used to amplify cDNA (FIG. 1). Circularized cDNA was then amplified using Phi29 and random hexamers to perform Rolling Circle Amplification (RCA). The resulting High Molecular Weight (HMW) DNA was then debranched using T7 Endonuclease and sequenced on the ONT MinION sequencer using the 1D sequencing kit (LSK108) kit and R9.5 flowcell (FLO-MIN107).

Figure 2:
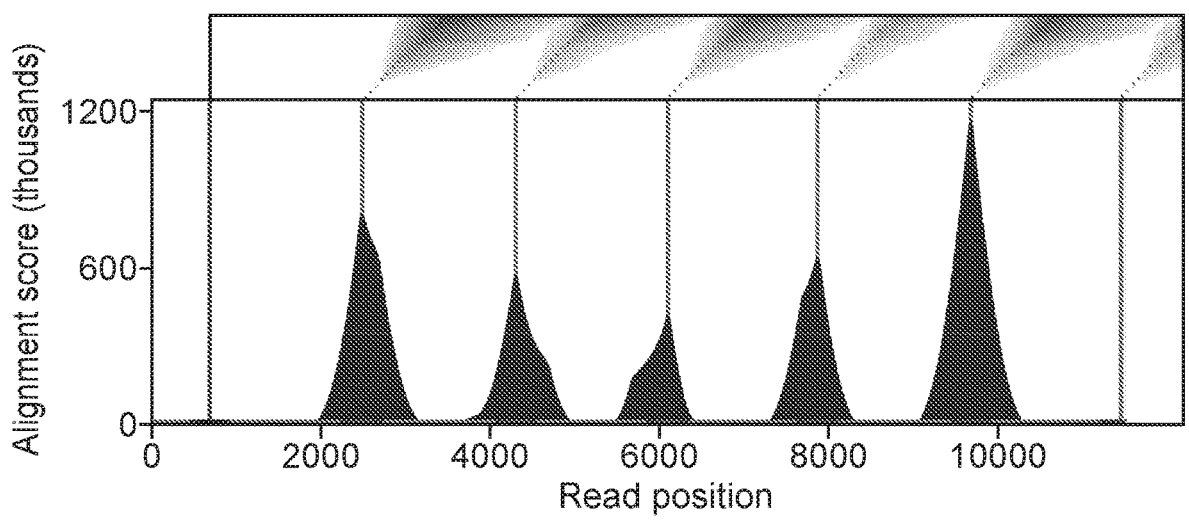
FIG. 2 Processing of raw reads into consensus reads of varying subread coverage according to one embodiment of the present disclosure. Panel A: Example of a 11.5 kb raw ONT read that was analyzed by our custom Smith-Waterman repeat finder. One initial splint (red line) is identified using the BLAT aligner, then modified Smith-Waterman self-to-self alignments are performed starting from the location of the initial splint. The score matrices (on top) are then processed to generate alignment score histograms (teal). Peaks (orange) are then called on these histograms. Complete subreads are then defined as the sequences between two peaks. Panel B: Cumulative number of SIRV E2 R2C2 consensus reads is plotted against their subread coverage. Panel C: PacBio Isoseq, standard ONT 1D, and $1D^2$ are compared to R2C2 at different subread coverage. Read accuracy is determined by minimap2 alignments to SIRV transcripts. Median accuracy is shown as a red line. Accuracy distribution is shown as a swarm plot of 250 randomly subsampled reads. Average raw read quality of ONT reads is indicated by the color of the individual points.
Figure 2:
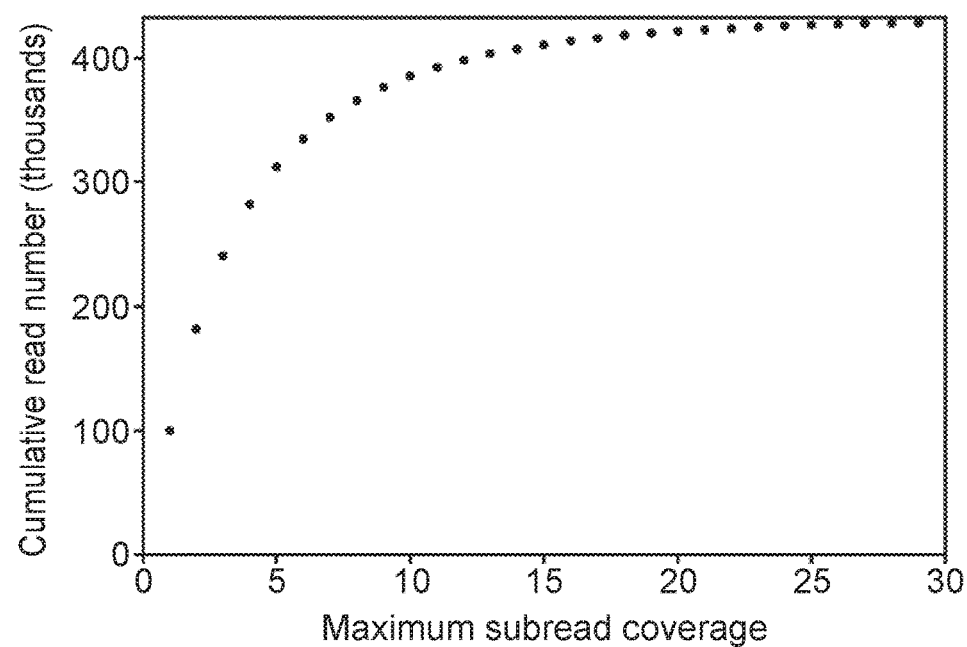
Figure 2:
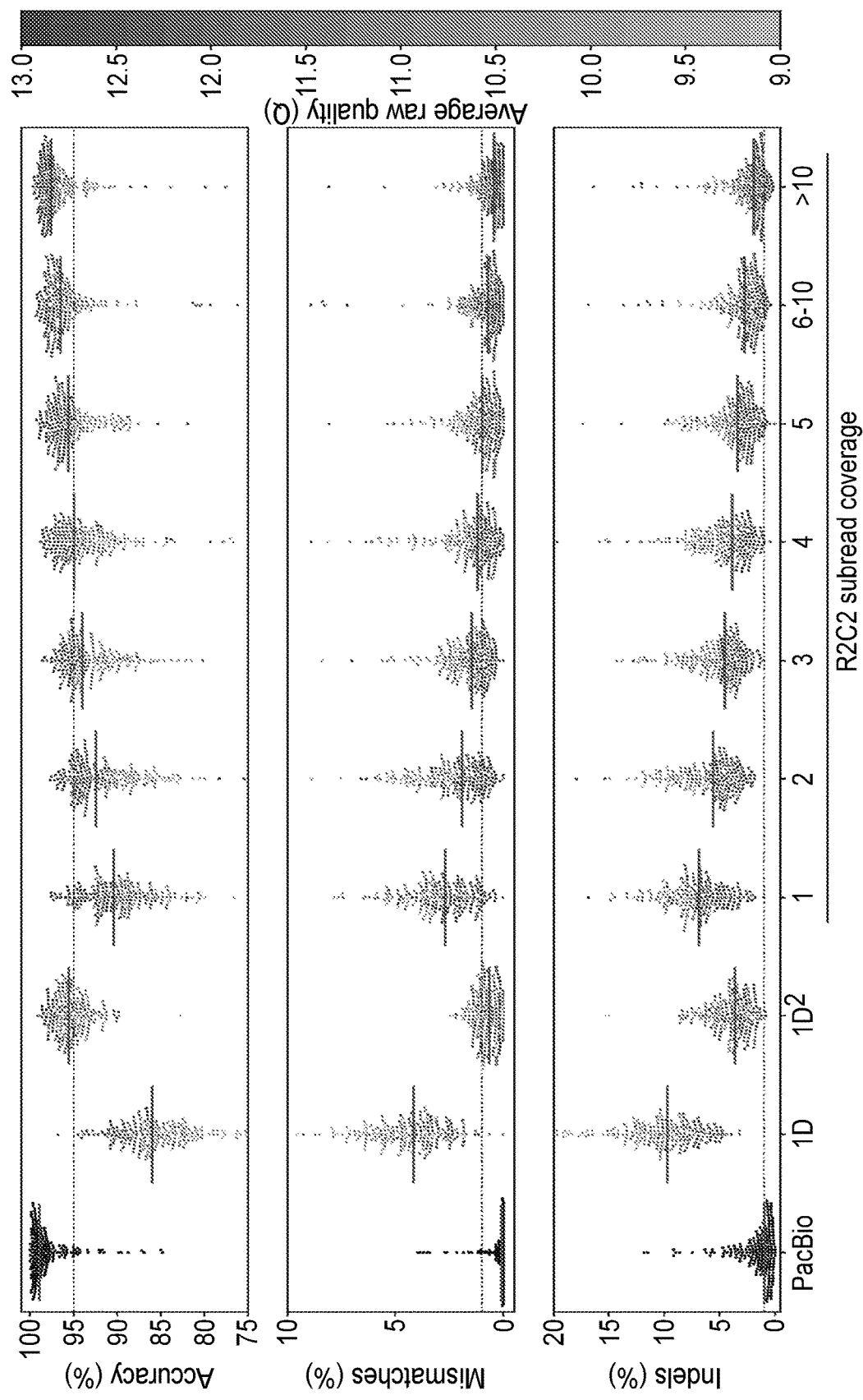

The sequencing run produced 828,684 reads with an average length of 5.0 kb resulting in a total base output of 4.1 Gb. For downstream analysis, 621,970 of these reads that were longer than 1 kb and had a raw quality score(Q) 9 were selected. Next, a computational workflow of the present method (designated as Concatemeric Consensus Caller using POA, or C3POa) was used to generate full-length cDNA consensus reads from the raw reads. C3POa detects DNA splint sequences raw reads using BLAT (14). Because BLAT is likely to miss DNA splint sequences in the noisy raw reads, each raw read for which BLAT found at least one DNA splint sequence was analyzed with a custom repeat finder which parses the score matrix of a modified Smith-Waterman self-to-self alignment (FIG. 1, FIG. 2 Panel A). Repeats, or subreads, are then combined into a consensus and error-corrected using poaV2 (15) and racon (16), respectively. Finally, only reads containing known priming sites at both cDNA ends are retained. In this way, C3POa generated 435,074 full-length cDNA consensus reads (and an additional 46,994 consensus reads from another multiplexed experiment) with varying subread coverage (Table 1, FIG. 2 Panels A and B).

TABLE 1

Run Statistics

| Run Type | cDNA source | Raw Base output (Gb) | Raw Read output | Raw reads with length > 1 kb and Q ≥ 9 | Full-length R2C2 Consensus reads |
|---|---|---|---|---|---|
| 1D | SIRV E2 | 4.15 | 828,684 | 621,970 | 435,074 |
| RAD4 | B cells | 2.06 | 408,347 | 227,250 | 149,791 |
| RAD4 | B cells | 3.59 | 583,192 | 356,245 | 248,546 |
| RAD4 | B cells | 4.23 | 877,412 | 528,800 | 345,402 |
| RAD4 | B cells | 4.75 | 1,004,208 | 593,086 | 388,968 |

Figure 3:
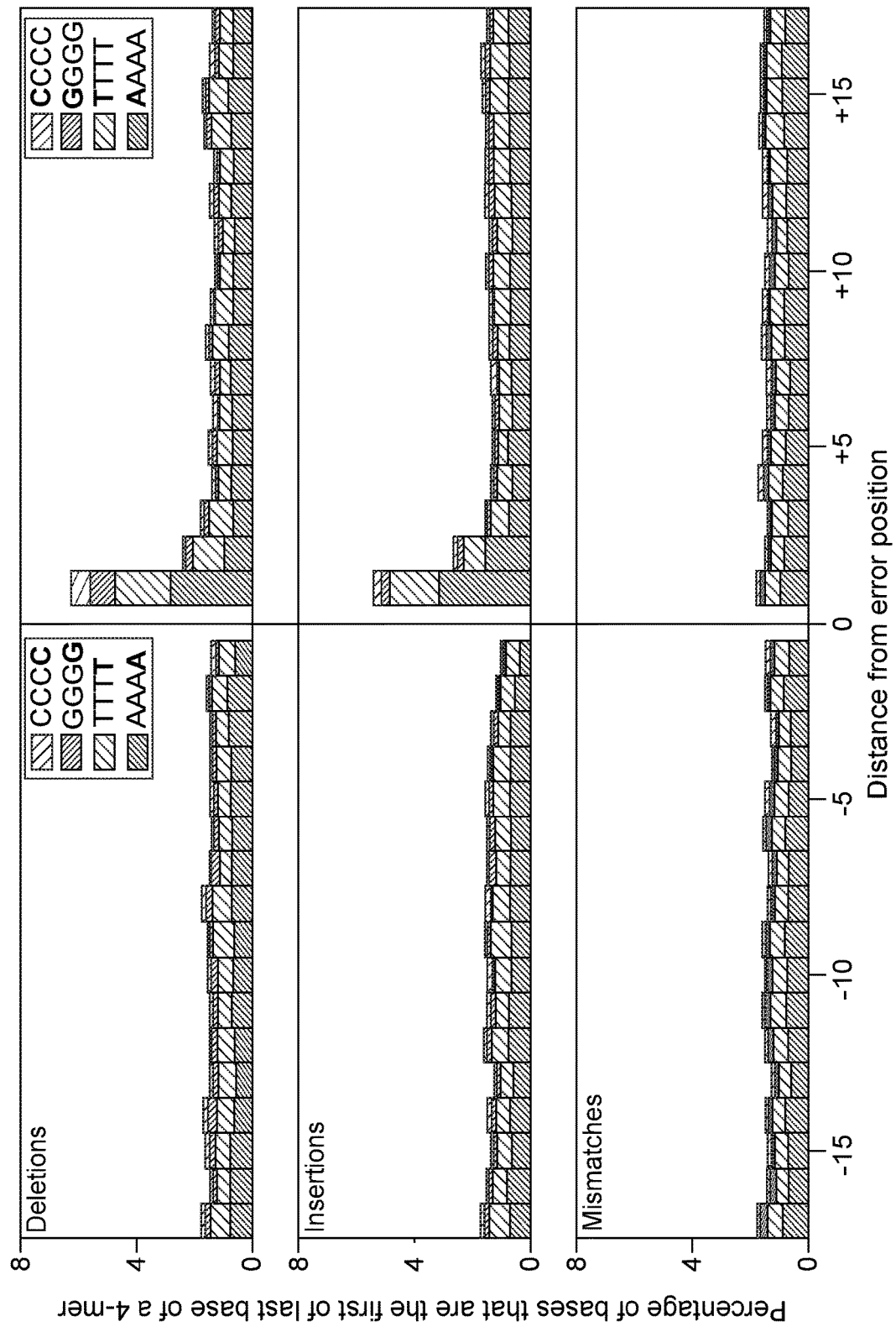
FIG. 3 Sequence context of error in reads. The occurrence of 4-mers (CCCC, GGGG, TTTT, or AAAA) around R2C2 sequencing deletions, insertions, and mismatches is shown as stacked bar plots for R2C2 reads covering SIRV cDNA (Panel A) or human B cell cDNA (aligned to hg38) (Panel B).
Figure 3:
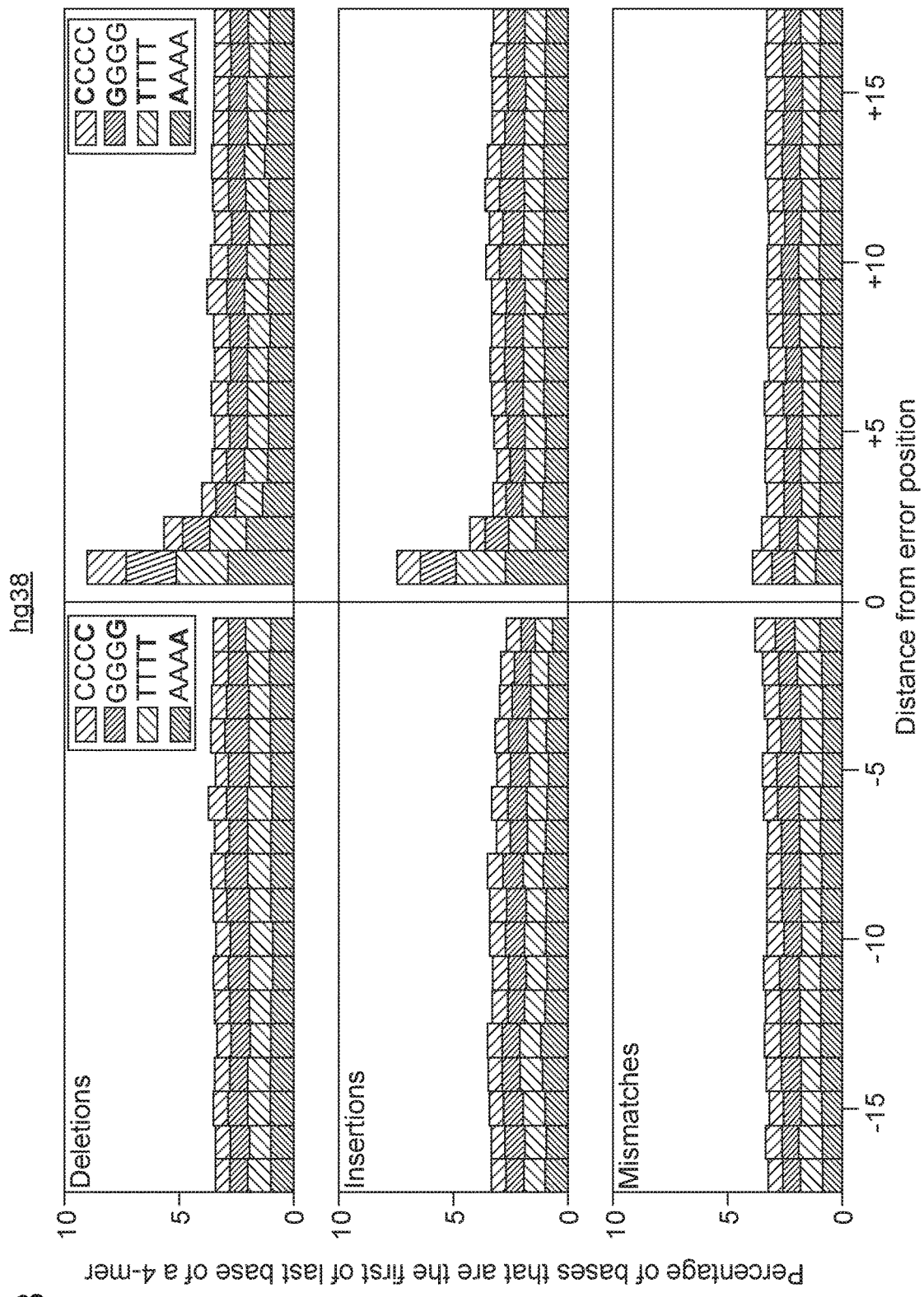

The same cDNA pool was also analyzed using a standard, heavily multiplexed ONT 1 D2 run generating 5,904 full-length 1D and 1,142 1 D2 cDNA reads, and the PacBio IsoSeq protocol generating 233,852 full-length cDNA Circular Consensus (CCS) reads. The resulting reads generated by each protocol were aligned to the SIRV transcript sequences using minimap2 and percent identity (accuracy) was calculated using those alignments. The 1D2 run produced reads with a median accuracy of 87% (1D reads) or 95.6% (1 D2 reads), while PacBio CCS reads had a median accuracy of 98.9%. R2C2 reads had a median accuracy of 94% (FIG. 2, Panel C) with the accuracy of individual R2C2 reads being highly correlated with average quality score of its underlying raw read as well as the numbers of subreads this raw read contained (FIG. 2, Panel C). While mismatch errors declined rapidly with increasing number of subreads, insertion and deletion errors declined more slowly. This might be explained by insertion and deletion errors not being entirely random but systematically appearing in stretches of the same base, i.e., homopolymers (8). Indeed, 4-mers ('AAAA', 'CCCC', 'TTTT', 'GGGG') were enriched around insertion and deletion errors in R2C2 consensus reads (FIG. 3). Overall, more aggressive filtering of R2C2 reads based on raw read quality score and subread coverage could increase the median accuracy of the R2C2 method but would also reduce overall read output.

Figure 4:
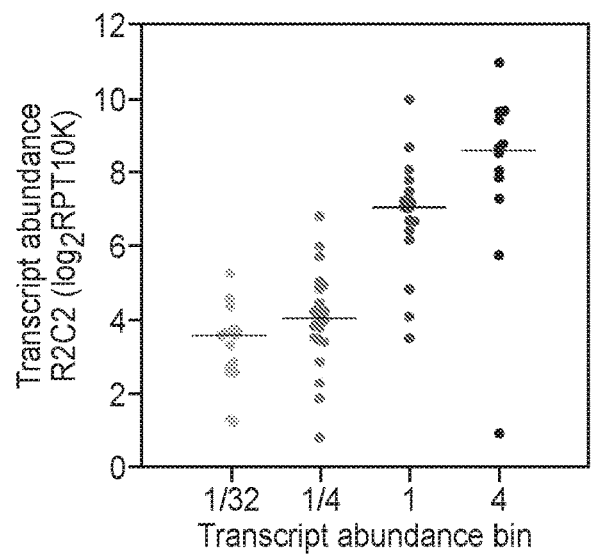
FIG. 4 R2C2 reads can quantify SIRV transcripts. R2C2 reads were aligned to SIRV transcripts using minimap2 and expression values transcript abundance determined as Reads Per Transcript Per 10K reads (RPG10K). The transcript count ratio was plotted on the y-axis against the nominal transcript abundance bin reported by the SIRV transcript manufacturer (Lexogen) (Panel A), the transcript length (Panel B), and transcript count ratio calculated from PacBio Isoseq reads (Panel C). Pearson correlation coefficient (r) is reported in Panel C. Each point represents a transcript and is colored according to it transcript abundance bin in all panels. Panel D: Genome browser view of Transcriptome annotation, isoforms identified by Mandalorion, and R2C2 consensus reads is shown of the indicated synthetic SIRV gene loci. Transcript and read direction is shown by colors (Blue: +strand, Yellow: −strand).
Figure 4:
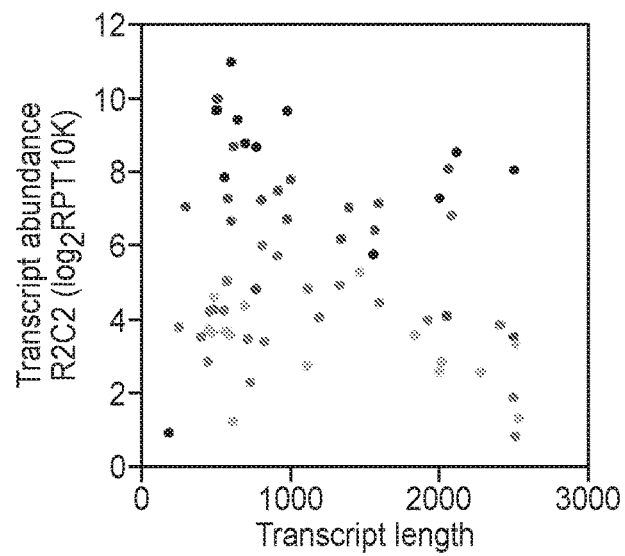
Figure 4:
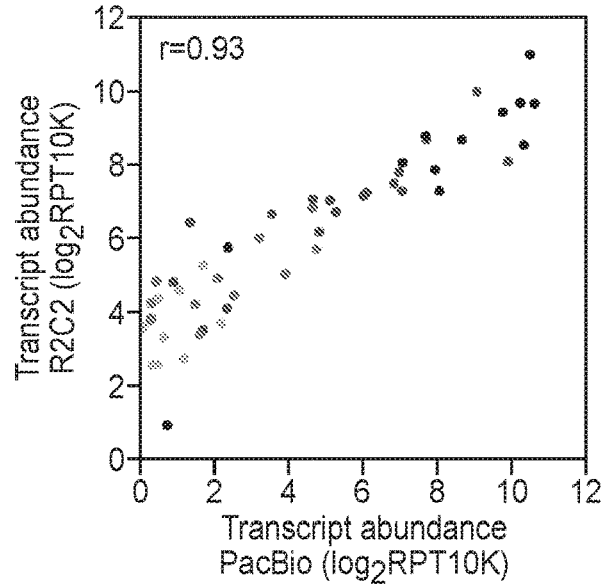
Figure 4:
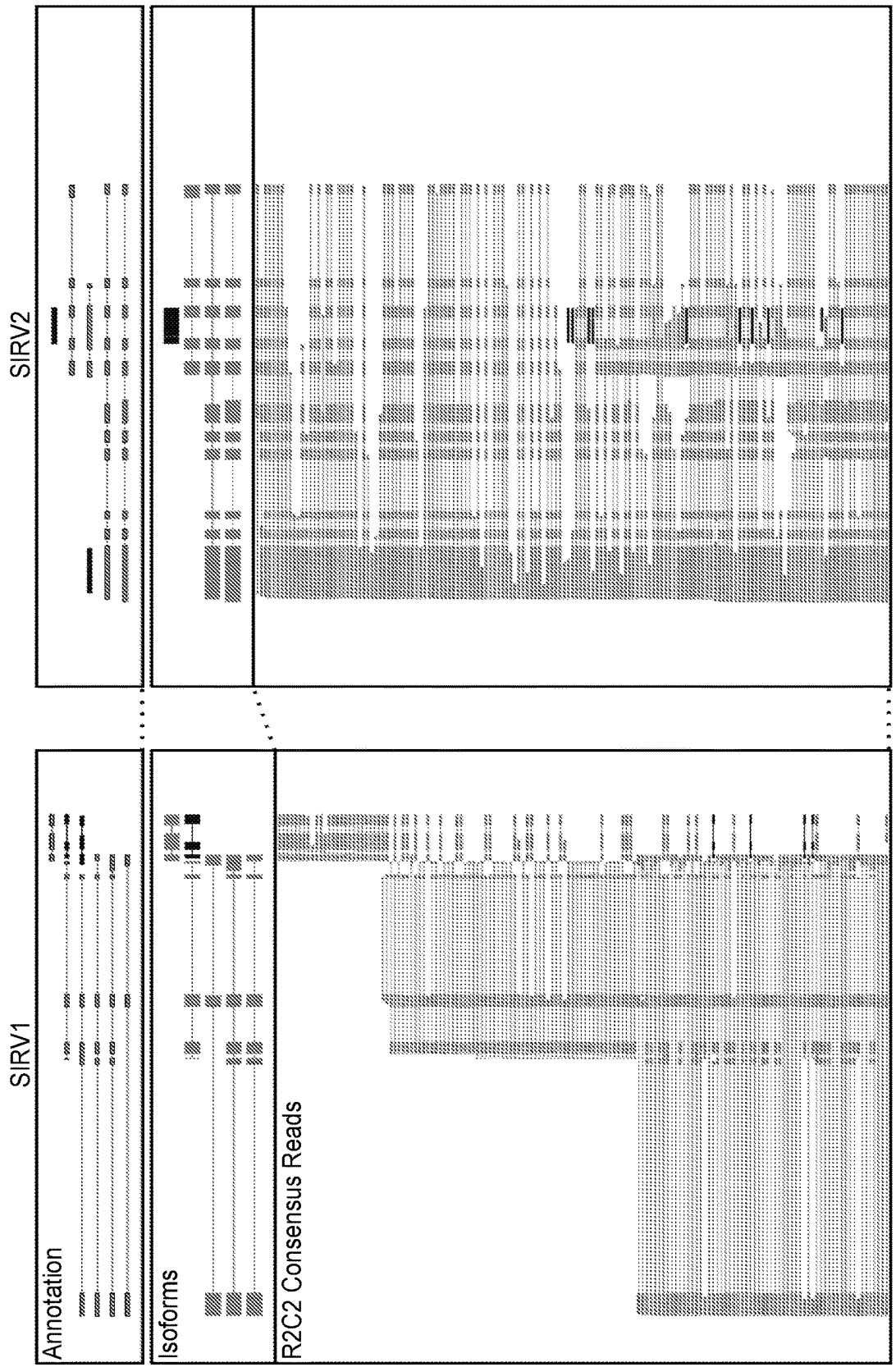

Example 2—R2C2 Correlates Well with PacBio for the Quantification of SIRV Transcripts SIRV E2 transcripts vary in length from ~0.3-2.5 kb and are provided in four nominal concentration bins ("1/32", "1/4", "1", "4") varying across two orders of magnitude. By analyzing the same SIRV E2 cDNA pools using R2C2 and PacBio IsoSeq, it was found that the R2C2 transcript counts generally matched nominal SIRV concentrations (FIG. 4, Panel A). Additionally, there seems to be no clear length bias (FIG. 4, Panel B), and the R2C2 transcript counts matched PacBio transcript counts very well with a Pearson correlation coefficient of 0.93 (FIG. 4, Panel C).

This indicates that the potential variation in transcript quantification seen in FIG. 4 (Panel A) were either rooted in differences in the initial RNA concentration found in the SIRV E2 mix or biases of the present modified Smart-seq2 based cDNA amplification step rather than new biases introduced by the sequencing technology.

Example 3—Simple and Accurate Isoform Identification

Next, it was tested whether the increased accuracy of R2C2 reads would benefit splice junction and isoform identification. To this end, PacBio, ONT and R2C2 reads were aligned to the artificial SIRVome sequence provided as a genome reference for their SIRV transcripts (FIG. 2, Panel D). 91% of splice junctions in R2C2 consensus reads matched annotated splice sites perfectly, far exceeding ONT 1D raw reads at 80% and approaching PacBio CCS reads at 96%.

Figure 5:
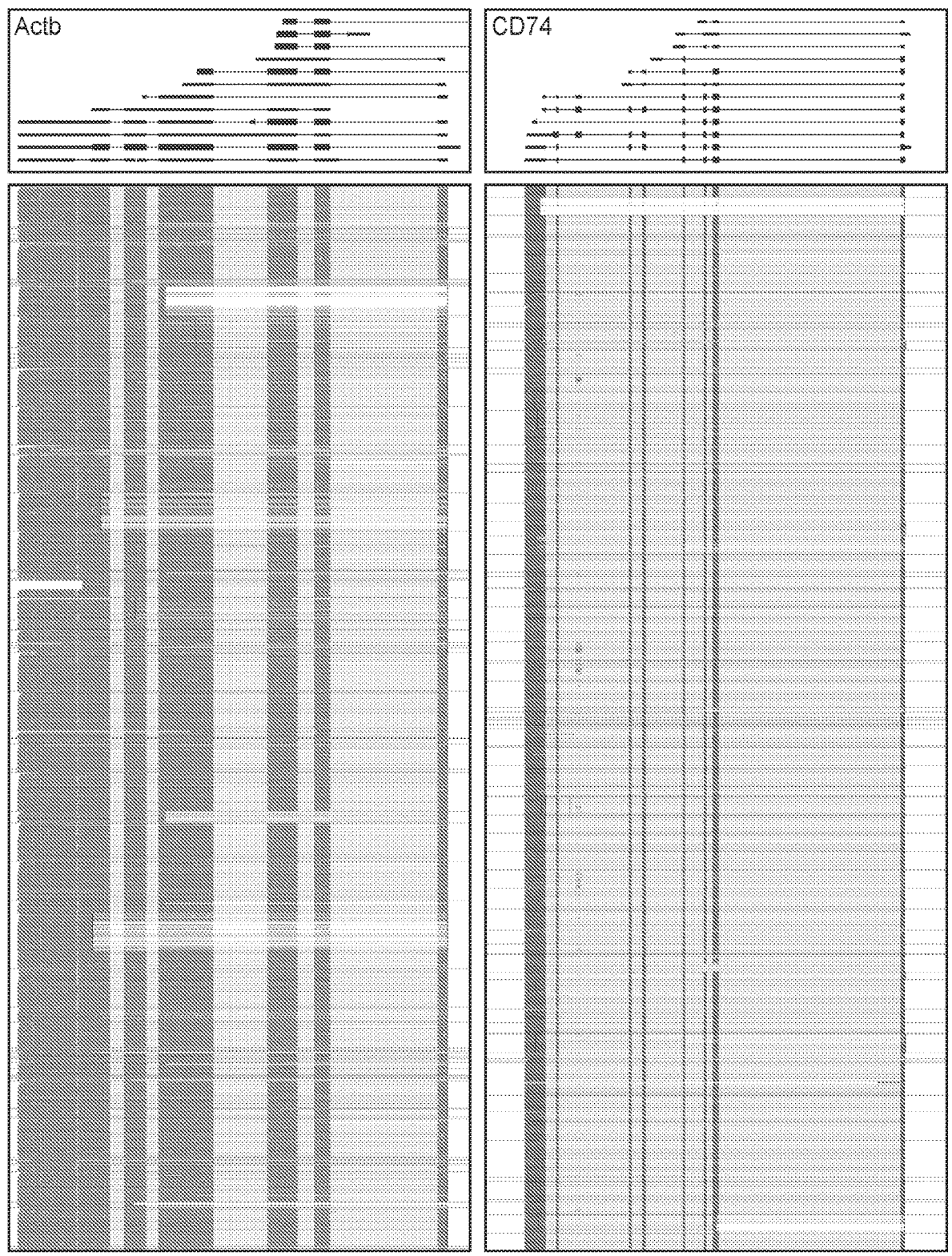
FIG. 5 Consensus reads of single cell cDNA. Genome browser view of Transcriptome annotation and up to 200

This increased accuracy allowed simplification of a Mandalorion pipeline for isoform identification (see Methods). To test how this new version of Mandalorion would perform, R2C2 consensus read alignments were subsampled to levels found in highly expressed genes in whole transcriptome analysis (500 read alignments per SIRV gene locus). Some of these subsampled R2C2 consensus reads did not align from end to end to a SIRV transcript (FIG. 2, Panel D). These may be products of cDNA synthesis of degraded RNA molecules likely caused by repeated freeze-thaw cycles of the SIRV E2 standards for they all contained complete 5' and 3' priming sites and adapter sequences. This highlighted the importance of RNA integrity for full-length transcriptome sequencing. Indeed, R2C2 reads created from single B cell lysates which are thawed only once immediately before cDNA synthesis showed evidence of degradation products at much lower levels (FIG. 5).

Because these degradation products appear to be largely random, they had little effect on the Mandalorion pipeline which identified 34 high confidence isoforms based on the subsampled R2C2 consensus reads (FIG. 2, Panel D). 24 of these isoforms matched annotated transcripts from the "1" and "4" abundance bins, while eight isoforms matched annotated transcripts from the "1/4" and "1/32" abundance bins. Only two high confidence isoforms represented truncated transcripts, caused by an oligodT mispriming on an A-rich region of the SIRV303 transcript, or a premature template switch on the (likely degraded) SIRV602 transcript, respectively. This indicated that R2C2 consensus reads paired with the Mandalorion pipeline can identify complex transcript isoforms.

Example 4—Demultiplexing of 7-8 nt Cellular Indexes

Next, it was tested whether R2C2 reads are accurate enough to demultiplex reads based on short cellular indexes like those employed by 10×, Drop-Seq or the inventors' own Tn5Prime single cell RNAseq protocols. To this end, the SIRV cDNA sequenced with the R2C2 method was indexed with 8 distinct combinations of a 7 nt (TSO) and a 8 nt (Nextera adapter) indexes. It was found that one 7 nt and one 8 nt index could confidently be assigned to 74% of R2C2 reads using a custom demultiplexing script based on Levenshtein distance between the observed sequence at the index position and the known input indexes. In 99.8% of the R2C2 assigned reads, it was found that the combination of identified indexes matched one of the distinct combinations present in the cDNA pool.

Example 5—Analysis of 96 Single B Cell Transcriptomes

Having established that the Tn5Prime data could be demultiplexed using R2C2 reads with very little crosstalk between samples, cDNA was sequenced from 96 single B cells previously analyzed using Illumina sequencing (13). To streamline the sequencing reaction, the ONT RAD4 (RAD004) kit was used, which has a lower average read output than the ligation based 1D kit but has a much shorter (~20 min) and, in the inventors' experience, more consistent and less error-prone workflow. Using the ONT RAD4 kit, 2,064,911 raw reads were generated across 4 sequencing runs using R9.5 flowcells. C3POa generated 1,132,707 full-length R2C2 consensus reads which matched the length distribution of the sequenced cDNA closely (FIG. 6, Panel A). 975,500 of the R2C2 consensus reads successfully aligned to the human genome and 730,023 of those aligned reads were assigned to single B cells based on their 7 nt and 8 nt cellular indexes. It was found that the vast majority of those reads were complete on the 5' end by comparing the alignment ends of these reads to transcription start sites (TSSs) previously identified (13) using Illumina sequencing. 653,410 of 730,023 (90%) reads either aligned to within 10 bp of a predicted TSS (604,940 reads) or aligned within a rearranged antibody locus (48,470 reads) which makes accurate read alignment impossible.

Example 6—Gene Expression Quantification in Single Human B Cells

Individual cells were assigned 7,604 reads on average. An average of 532 genes were detected per cell (at least one R2C2 consensus read overlapping with the gene). Both the numbers of genes detected as well as gene expression quantification based on these R2C2 consensus reads closely matched RNAseq-based quantification (13). When comparing gene expression of the same cell, RNAseq and R2C2 quantification had a median pearson correlation coefficient (r) of 0.79 opposed to 0.14 when comparing different cells with one another (FIG. 6, Panel B). Using t-SNE clustering on R2C2 and Illumina data resulted in the sub-clustering of the same J chain-positive cells which were previously identified as plasmablasts (as opposed to memory B cells) (FIG. 6, Panel C).

Example 7—Identification of Isoforms in Single Human B Cells

An updated Mandalorion pipeline was used to identify high confidence isoforms separately for each of the 96 B cells analyzed. By grouping R2C2 consensus reads based on their splice sites and alignment starts and ends, Mandalorion identified an average of 163 high confidence isoforms per cell. It was found that identification of high confidence isoforms was dependent upon R2C2 consensus read coverage. At least one isoform was identified in 3.1%, 64.9%, 92.2% of genes covered by 1-4 reads, 5-9 reads, or >10 reads, respectively. The vast majority of genes with >10 R2C2 consensus reads contained one (78%) or two (11%) isoforms, highlighting the low complexity of single cell transcriptomes.

Figure 7:
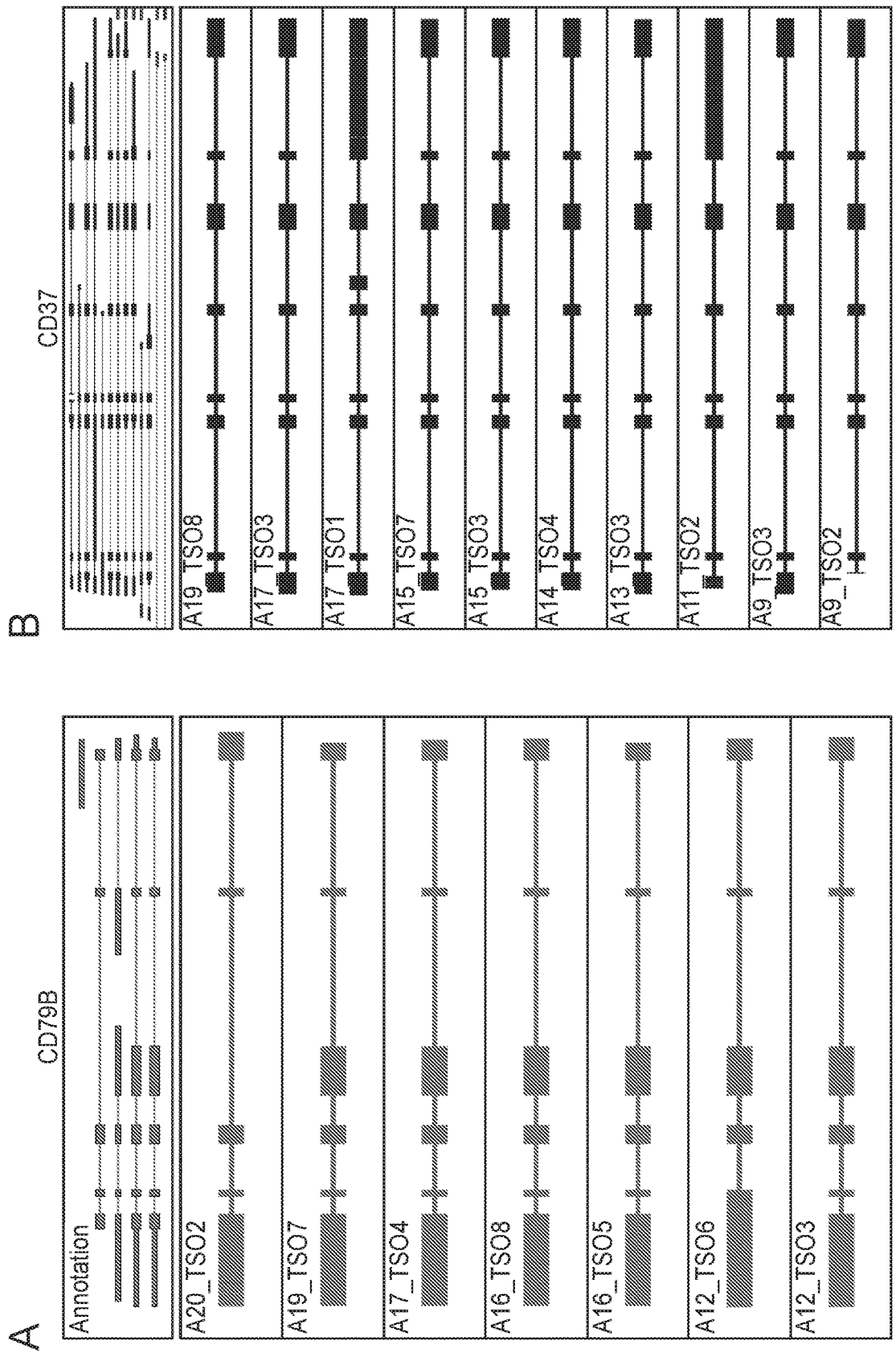
Figure 7:
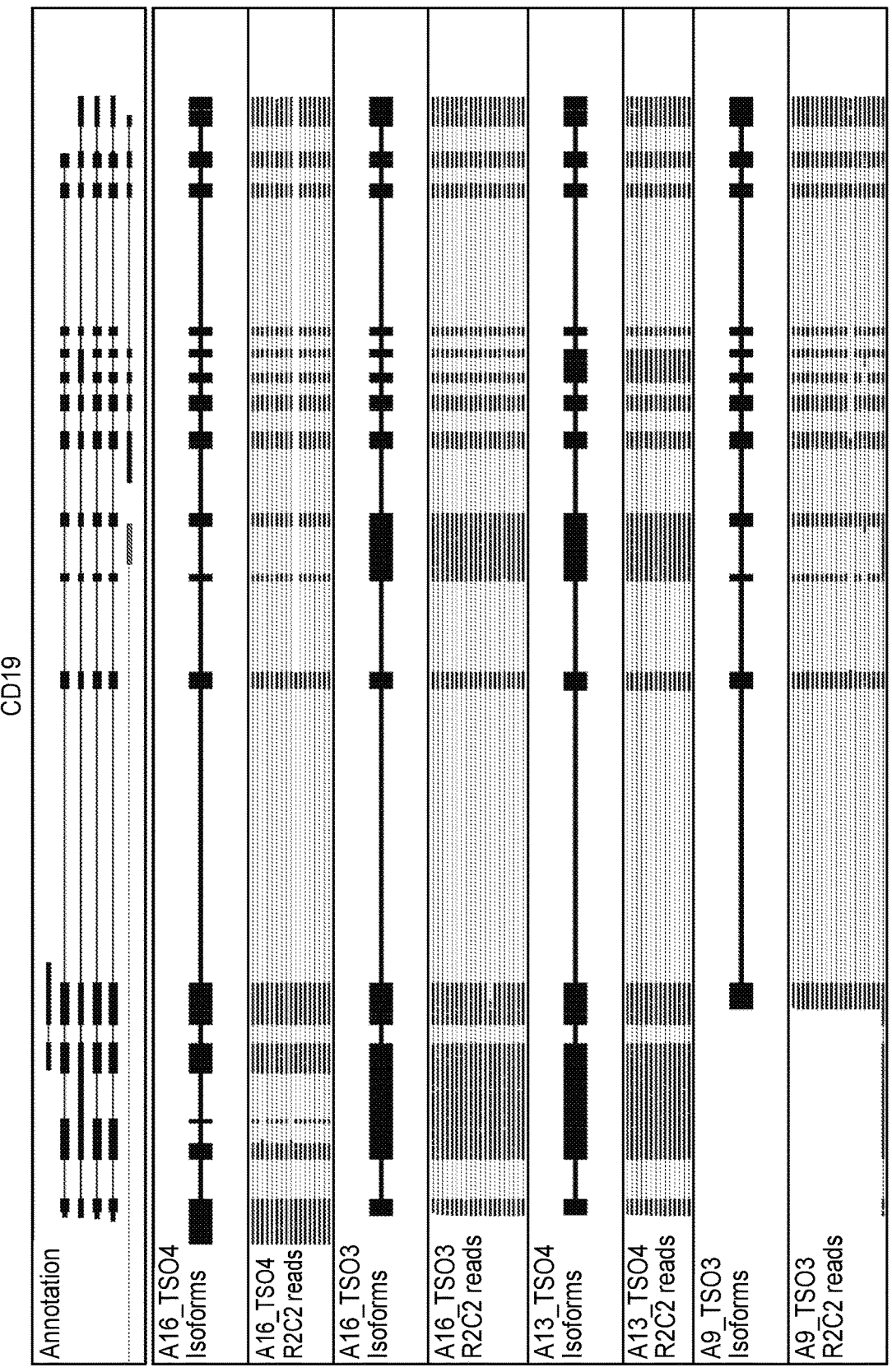

Overall, the isoforms identified had a 99.1% sequence similarity with the human genome. As previously observed for mouse B1 cells (7), human B cells show a diverse array of isoforms across their surface receptors. CD37 and CD79B, which were expressed in several B cells, showed diverse isoforms. These isoforms were defined by 1) intron retention events (CD79B: Cell A12_TSO6, CD37: Cells A11_TSO2 and A17_TSO1), 2) variable transcription start sites (TSSs), and alternatively spliced exons (CD79B: Cell A20_TSO2, CD37: Cell A17_TSO1), with the alternatively spliced exon being only partially annotated (FIG. 7).

Finally, for the B cell defining CD19 receptors, also observed were multiple isoforms across cells, which is of particular interest because CD19 is a target for CAR T-cell therapy. Alternative splicing of CD19 has been shown to confer therapy resistance to B cell lymphomas. Interestingly, when the 4 identified isoforms were reference corrected (squanti-qc (17)) and translated, only one contained the epitope required for FMC63 based CAR T-cell therapy (FIG. 7, FIG. 8) (10-12).

While RNAseq analysis has fundamentally changed how transcriptional profiling is performed, it is ultimately a stop-gap solution born from the limitations of short-read sequencing technologies. The need to fragment transcripts to fit short-read technologies like Illumina results in often unsurmountable analysis challenges. As a result, RNAseq analysis is often used like gene expression microarrays with the data used for downstream analysis being gene-expression values. Single cell RNAseq has further exacerbated this limitation because it is often restricted to 3' or 5' tag counting and generates gene expression values that are sparse due to both biological and technical reasons.

This results in a loss of information because individual genes can express many different isoforms, often with different functions. However, many bulk and single cell RNAseq methods do generate full-length cDNA as an intermediate product in library preparation. Long-read technology is able to take advantage of this full-length cDNA. While long-read sequencing technologies do not currently match Illumina's read output and accuracy, their outputs and accuracies are increasing. In the present study, over 200,000 reads were produced at close to 99% accuracy per run using the PacBio Sequel. Further, the standard ONT $1D^2$ protocol generated 1 million 1D cDNA reads at 87% accuracy and 50,000 1 $D^2$ reads at 95% accuracy in a single run. The nanopore-based R2C2 sequencing method described herein takes advantage of this high throughput and increases ONT read accuracy. The R2C2 method offers a compromise between PacBio and ONT technologies that generates on average 316,000 full-length cDNA reads at 94% accuracy in a single run. While the per run cost of flowcells and reagents of PacBio and ONT are roughly comparable, the capital cost of the PacBio Sequel sequencer (1300 k) vastly exceeds the cost of the ONT MinION (~$1 k). This effective lack of capital costs associated with the ONT-based R2C2 method results in much lower total cost of accurate full-length transcriptome analysis compared to the PacBio IsoSeq workflow. Indeed, at its current throughput and accuracy and combined with the low cost of the ONT MinION, R2C2 brings comprehensive full-length transcriptome analysis within reach of most molecular biology laboratories.

The R2C2 method is a suitable complement for short-read sequencing. To this end, the R2C2 can be easily adapted to any RNAseq library preparation protocol that produces full-length double stranded cDNA molecules with known adapter/primer sequences at their ends. This includes standard Smart-seq2, 10× Genomics, and Drop-seq protocols. Adapting R2C2 to these protocols only requires the generation of a compatible DNA splint by modifying the primers used for amplifying the DNA splint. The same cDNA pool can then be sequenced by both Illumina and R2C2 methods.

R2C2 can replace short-read RNAseq and its shotgun approach to transcriptome analysis, especially considering the impending wide release of the high-throughput ONT Prometh ION sequencer. This will be a significant advance considering the strength of full-length transcriptome sequencing showcased here. R2C2 paired with Mandalorion accurately identified full-length synthetic transcripts as well as several surface receptor isoforms of CD79B, CD37, and CD19 expressed by 96 distinct single human B cells. Identifying these full-length isoforms with short read RNAseq would have been impossible. Finally, the CD19 RNA isoforms identified in the present study in the single B cells derived from a healthy adult may have implications regarding immunotherapy efficacy for most lacked the epitope in exon 4 that is targeted by FMC63 based CAR T-cell therapy. This confirms that even healthy individuals contain RNA isoform diversity for CD19 which may ultimately contribute to immunotherapy resistance when undergoing FMC63 based CAR T-cell therapy (10, 11).

Methods 100 pg of SIRV E0 (Lexogen) RNA or lysed single B cells (Collected from the blood of a fully consented healthy adult in a study approved by the Institutional Review Board (IRB) at UCSC) were amplified using the Tn5Prime(18) method, which represents a modification of the Smart-seq2 (19, 20) method developed to capture 5' ends of transcripts using Illumina sequencing.

This method uses distinct template switch oligo (TSO) and oligodT primer sequences, enabling the easy differentiation of transcript 5' and 3' ends when using long-read sequencing. Following the Tn5Prime protocol, RNA or Single Cell Lysate were reverse transcribed (RT) using Smartscribe Reverse Transcriptase (Clontech) in a 10 ul reaction including an oligodT primer and a Nextera A TSO containing a 7 nucleotide sample index (Table 51). RT was performed for 60 min at 42° C. The resulting cDNA was treated with 1 ul of 1:10 dilutions of RNAse A (Thermo) and Lambda Exonuclease (NEB) for 30 min at 37° C. The treated cDNA was then amplified using KAPA Hifi Readymix 2× (KAPA) and incubated at 95° C. for 3 mins, followed by 15 cycles for SIRV RNA or 27 cycles (single B cells) of (98° C. for 20 s, 67° C. for 15 s, 72° C. for 4 mins), with a final extension at 72° C. for 5 mins. cDNA amplification requires both the ISPCR primer and a Nextera A Index primer, which contains another 8 nucleotide sample index.

SIRV RNA: 8 SIRV E2 RNA aliquots were reverse transcribed and amplified in separate reactions adding distinct 7 nucleotide TSO and 8 nucleotide Nextera A Indexes to each resulting cDNA aliquot. The separate aliquots used directly as input into our R2C2 method or amplified using KAPA Hifi Readymix 2× (KAPA) (95° C. for 3 mins, followed by 15 cycles (98° C. for 20 s, 67° C. for 15 s, 72° C. for 4 mins), with a final extension at 72° C. for 5 mins with ISPCR and Nextera_A_Universal Primers and pooled at equal amounts for input into PacBio Iso-Seq pipeline at the University of Georgia Athens sequencing core.

Single B cell lysates: Single B cells in separate in the wells of a 96 well plate were reverse transcribed using a distinct 7 nucleotide TSO index for each row. Columns were then pooled and amplified, using a distinct 8 nucleotide Nextera A Index for each pool. This resulted in the cDNA of all 96 cells carrying a unique combination of TSO and Nextera A index. This cDNA was then pooled for Illumina sequencing (HiSeq4000 2×150) (13) or amplified using KAPA Hifi Readymix 2× (KAPA) (95° C. for 3 mins, followed by 15 cycles (98° C. for 20 s, 67° C. for 15 s, 72° C. for 4 mins), with a final extension at 72° C. for 5 mins with ISPCR and Nextera_A_Universal Primers for input into our R2C2 method.

DNA Splint Amplification

A ~200 bp DNA splint to enable Gibson Assembly (21) circularization of cDNA was amplified from Lambda DNA using KAPA Hifi Readymix 2× (KAPA) (95° C. for 3 mins, followed by 25 cycles (98° C. for 20 s, 67° C. for 15 s, 72° C. for 30 s) using primer Lambda_F_ISPCR(RC) and Lambda_R_NextA(RC) (Table 51). This generated a double stranded DNA with matching overlaps to full-length cDNA.

R2C2 Sample Preparation

Circularization of cDNA 200 ng of cDNA was mixed with 200 ng of DNA splint. Volume was adjusted to 6 ul and 6 μl of 2× NEBuilder Hifi DNA Assembly Master Mix (NEB). The reaction was incubated for 60 min at 55° C. Volume was adjusted to 20 μl and non-circularized DNA was digested using 1 μl of 1:10 Exonuclease III and Lambda Exonuclease as well as 1 μl of Exonuclease I (all NEB). Circularized DNA was extracted using SPRI beads with a size cutoff to eliminate DNA <500 bp (0.8 beads:1 sample) and eluted in 50 μl of ultrapure water.

Rolling Circle Amplification Circularized DNA was split into 5 aliquots of 10 μl and each aliquot was amplified in its own 50 μl reaction containing Phi29 polymerase (NEB) and exonuclease resistant random hexamers (Thermo) (5 μl of 10× Phi29 Buffer, 2.5 μl of 10 μM (each) dNTPs, 2.5 μl random hexamers (10 μM), 10 μl of DNA, 29 μl ultrapure water, 1 μl of Phi29). Reaction were incubated 30° C. overnight. All reaction were pooled and volume was adjusted to 300 μl with ultrapure water. DNA was extracted using SPRI beads with a size cutoff to eliminate DNA <2000 bp (0.5 beads:1 sample). At this point the High Molecular Weight DNA can easily shear. Therefore, beads and samples were mixed by gentle flicking of the tube, not vortexing or vigorous pipetting. Beads were allowed to settle for 5 min on magnet, and after two 70% Ethanol washes, a mix of 90 μl of ultrapure water, 10 μl NEB buffer 2 and 5 μl T7 Endonuclease was added to the beads. Beads were incubated for 2 hour on a thermal shaker at 37° C. under constant agitation. Beads were then placed on magnet and supernatant is recovered. The DNA in the supernatant is then extracted again using SPRI beads with a size cutoff to eliminate DNA <2000 bp (0.5 beads:1 sample) and eluted in 15 μl of ultrapure water.

1 μl of the eluate was diluted in 19 μl of ultrapure water. 1 μl of the 1:20 dilution was used to determine the concentration of the eluate using a Qubit High Sensitivity DNA kit (Thermo). The other 19 μl were analyzed on a 1% agarose gel. Successful RCA and debranching by T7 Endonuclease results in HMW DNA that runs above the 10 kb band of the NEB 2-log ladder but is not stuck in the loading well.

Nanopore Sequencing

SIRV E2 RCA product was sequenced using the ONT 1D sample prep kit and a single 9.5 flowcell according to manufacturer's instructions with the exception that DNA was not sheared prior to library prep. Single B cell RCA product was sequencing using the ONT RAD4 kit and four 9.5 flowcells. The resulting raw data was basecalled using the albacore (version 2.1.3) read_fast5_basecaller script with the following settings:

1D Run:
    read_fast5_basecaller.py -r --flowcell FLO-MIN107 --kit SQK-LSK108 --output_format fastq --input/path/to/raw_data --save_path/path/to/output_folder --worker_threads 20

Rad4 Runs:
    read_fast5_basecaller.py -r --flowcell FLO-MIN107 --kit SQK-RAD004 --output_format fastq --input/path/to/raw_data --save_path/path/to/output_folder --worker_threads 20

C3POa Data Processing

Pre-Processing (C3POa_Preprocessing.Py)

Basecalled raw reads underwent pre-processing to shorten read names and remove short (<1000 kb) and low quality reads (Q<9) reads. Raw reads were first analyzed using BLAT (14) to detect DNA splint sequences. If one or more splint sequences were detected in a raw read, the raw read underwent consensus calling.

Consensus Calling (C3POa.Py)

Tandem repeats were identified in each raw read using a modified Smith Waterman self-to-self alignment. A 1000 nucleotide long subsequence adjacent to the splint was aligned to the entire raw read. All lines parallel to the diagonal were summed. Peaks were then called along these values which indicate the position of the other splint sequences in the tandem repeats the raw read contains (FIG. 1, Panel B).

Raw reads are then split into complete subreads containing full repeats and incomplete subreads containing partial repeats at the read ends. If there are more than 1 complete subreads, these complete subreads are aligned using poaV2 (15) with the following command:

poa -read fasta_path/to/subreads.fasta -hb -pir path/to/alignments.pir -do_progressive NUC.4.4.mat >./poa_messages. txt 2>&1

The preliminary consensus is either reported by poaV2 (more than 2 subreads) or determined based on the poaV2 alignment by a custom script taking raw read quality scores into account (2 subreads). If only one complete subread is present in the raw read, its sequenced is used as consensus in the following steps.

Complete and incomplete subreads are aligned to the consensus sequence using minimap2 (25) and the following command minimap2 --secondary=no -ax map-ont path/to/consensus.fasta path/to/subreads.fastq >path/to/subread_overlap.sam 2>./minimap2_messages.txt These alignments are used as input to the racon (16) algorithm which error-corrects the consensus.

racon --sam --bq 5 -t 1 path/to/subreads.fastq path/to/subread_overlap.sam path/to/consensus. fasta path/to/corrected_consensus. fasta >./racon_messages. txt 2>&1

Post-Processing (C3POa Postprocessing.Py)

ISPCR and Nextera Sequences are identified by BLAT and the read is trimmed to their positions and reoriented to 5'->3'.

Alignment

Trimmed, full-length R2C2 reads and PacBio reads are aligned to the appropriate genomes and transcripts using minimap2. The following settings were used when:

Aligning to SIRV Transcript Sequences:
    minimap2 --secondary=no -ax map-ont /path/to/SIRV_Transcriptome_nopolyA.fasta path/to/trimmed_corrected_consensus.fasta >path/to/aligned.out.sirv.sam Aligning to the "SIRVome" Sequences:
    minimap2 --splice-flank=no --secondary=no -ax splice/path/to/SIRVome.fasta path/to/trimmed_corrected_consensus.fasta >path/to/aligned.out.sirvome.sam Aligning to the Human Genome (Only Chromosomes, No Alternative Assemblies, etc. . . . ):
    minimap2 --secondary=no -ax splice/path/to/hg38_chromosomes_only. fasta path/to/trimmed_corrected_consensus.fasta >path/to/aligned. out. hg38. sam Percent identity of sequencing reads were calculated from minimap2 alignments. First md strings were added to the sam files generated by minimap using samtools calmd functionality.

Matches, mismatches and indels are then calculated based on CIGAR and md string and percent identity is reported as (matches/(matches+mismatches+indels))*100.

For isofom identification and visualization SAM files were converted to PSL file format using the jvarkit sam2psl (26) script.

Isoform Identification and Quantification

Isoforms were identified and quantified using a new version of the Mandalorion pipeline (Ell) with the following settings:

Isoform Identification:
    python3 Mandalorion_define_and_quantify_isoforms.py -c path/to/content_file -p path/to/output/ -u 5 -d 30 -s 200 -r 0.05 -R 3 -i 0 -t 0 -l 100 -T 60 -g /path/to/genome_annotation.gtf Isoform Alignment:
    gmap -f psl -B 5 -t 6 -n 1 -d/path/to/human_reference_index path/to/isoform_consensi.fasta >path/to/isoform_consensi.psl Oligos All oligos are shown 5'->3' and were ordered from Integrated DNA Technologies (IDT). Lower case 'r' indicates RNA bases. Spaces in sequences are for visual emphasis only.

cDNA Generation

---

```
Reverse Transcription

>Oligo-dT-smartseq2
5Me-
isodC/AAGCAGTGGTATCAACGCAGAGTACTTTTTTTTTTTTTTTTTTTTTTTTTTTTT
(SEQ ID NO: 1)
```

-continued

```
>TSO1_Nextera
TCGTCGGCAGCGTCAGATGTGTATAAGAGArCAG rUGA ArU rUC
TGGTrGrGrG (SEQ ID NO: 2)

>TSO2_Nextera
TCGTCGGCAGCGTCAGATGTGTATAAGAGArCAG ACrU CrU GrU
TGGTrGrGrG (SEQ ID NO: 3)

>TSO3_Nextera
TCGTCGGCAGCGTCAGATGTGTATAAGAGArCAG CrUC rUG rUA
TGGTrGrGrG (SEQ ID NO: 4)

>TSO4_Nextera
TCGTCGGCAGCGTCAGATGTGTATAAGAGArCAG rUAG rUA CrU
TGGTrGrGrG (SEQ ID NO: 5)

>TSO5_Nextera
TCGTCGGCAGCGTCAGATGTGTATAAGAGArCAG GGrU CrU rUG
TGGTrGrGrG (SEQ ID NO: 6)

>TSO6_Nextera
TCGTCGGCAGCGTCAGATGTGTATAAGAGArCAG ArUA GrU ArU
TGGTrGrGrG (SEQ ID NO: 7)

>TSO7_Nextera
TCGTCGGCAGCGTCAGATGTGTATAAGAGArCAG rUCC rUA rUC
TGGTrGrGrG (SEQ ID NO: 8)

>TSO8_Nextera
TCGTCGGCAGCGTCAGATGTGTATAAGAGArCAG CArU rUC GrU
TGGTrGrGrG (SEQ ID NO: 9)
``` cDNA Amplification

```
>ISPCR
AAGCAGTGGTATCAACGCAGAGT (SEQ ID NO: 10)

>Nextera_Primer_A
AATGATACGGCGACCACCGAGATCTACAC [8 bp i5 index]
TCGTCGGCAGCGTCAGATG (SEQ ID NO: 11)
```

Splint Generation

```
>Lambda_F_ISPCR
ACTCTGCGTTGATACCACTGCTT AAAGGGATATTTTCGATCGCTTG (SEQ ID
NO: 12)

>Lambda_R_NextA
ATCTCGGTGGTCGCCGTATCATT TGAGGCTGATGAGTTCCATATTTG (SEQ ID
NO: 13)
```

All oligos are shown 5' 4 3' and were ordered from Integrated DNA Technologies (IDT). Lower case 'r' indicates RNA bases. Spaces in sequences are for visual emphasis only.

Further details regarding the present Examples section may be found in Volden et al. (2018) PNAS 115(39):9726-9731, the disclosure of which is incorporated herein by reference in its entirety for all purposes.

REFERENCES

1. Mortazavi A, Williams B A, McCue K, Schaeffer L, Wold B (2008) Mapping and quantifying mammalian transcriptomes by RNA-Seq. Nat Methods 5(7):621-628.
2. Tilgner H, et al. (2015) Comprehensive transcriptome analysis using synthetic long-read sequencing reveals molecular co-association of distant splicing events. Nat Biotechnol 33(7):736-742.
3. Tilgner H, et al. (2017) Microfluidic isoform sequencing shows widespread splicing coordination in the human transcriptome. Genome Res. doi:10.1101/gr.230516.117.
4. Sharon D, Tilgner H, Grubert F, Snyder M (2013) A single-molecule long-read survey of the human transcriptome. Nat Biotechnol 31(11):1009-1014.
5. Shi L, et al. (2016) Long-read sequencing and de novo assembly of a Chinese genome. Nat Commun 7:12065.
6. Kuo R I, et al. (2017) Normalized long read RNA sequencing in chicken reveals transcriptome complexity similar to human. BMC Genomics 18(1):323.
7. Byrne A, et al. (2017) Nanopore long-read RNAseq reveals widespread transcriptional variation among the surface receptors of individual B cells. Nat Commun 8:16027.
8. Oikonomopoulos S, Wang Y C, Djambazian H, Badescu D, Ragoussis J (2016) Benchmarking of the Oxford Nanopore MinION sequencing for quantitative and qualitative assessment of cDNA populations. Sci Rep 6:31602.
9. Li C, et al. (2016) INC-Seq: accurate single molecule reads using nanopore sequencing. Gigascience 5(1):34.
10. Sotillo E, et al. (2015) Convergence of Acquired Mutations and Alternative Splicing of CD19 Enables Resistance to CART-19 Immunotherapy. Cancer Discov 5(12):1282-1295.

11. Fischer J, et al. (2017) CD19 Isoforms Enabling Resistance to CART-19 Immunotherapy Are Expressed in B-ALL Patients at Initial Diagnosis. *J Immunother* 40(5):187-195.
12. Sommermeyer D, et al. (2017) Fully human CD19-specific chimeric antigen receptors for T-cell therapy. *Leukemia* 31(10):2191-2199.
13. Cole C, Byrne A, Beaudin A E, Forsberg E C, Vollmers C (2018) Tn5Prime, a Tn5 based 5' capture method for single cell RNA-seq. *Nucleic Acids Res*. doi:10.1093/nar/gky182.
14. Kent W J (2002) BLAT—The BLAST-Like Alignment Tool. *Genome Res* 12(4):656-664.
15. Lee C, Grasso C, Sharlow M F (2002) Multiple sequence alignment using partial order graphs. *Bioinformatics* 18(3):452-464.
16. Vaser R, Sović I, Nagarajan N, Šikić ~ M (2017) Fast and accurate de novo genome assembly from long uncorrected reads. *Genome Res* 27(5):737-746.
17. Tardaguila M, et al. (2017) SQANTI: extensive characterization of long read transcript sequences for quality control in full-length transcriptome identification and quantification. *bioRxiv*:118083.
18. Cole C, Byrne A, Beaudin A E, Camilla Forsberg E, Vollmers C (2017) Tn5Prime, a Tn5 based 5' Capture Method for Single Cell RNA-seq. *bioRxiv*:217117.
19. Picelli S, et al. (2014) Full-length RNA-seq from single cells using Smart-seq2. *Nat Protoc* 9(1):171-181.
20. Picelli S, et al. (2014) Tn5 transposase and tagmentation procedures for massively scaled sequencing projects. *Genome Res* 24(12):2033-2040.
21. Gibson D G, et al. (2009) Enzymatic assembly of DNA molecules up to several hundred kilobases. *Nat Methods* 6(5):343-345.
22. Li W, et al. (2015) The EMBL-EBI bioinformatics web and programmatic tools framework. *Nucleic Acids Res* 43(W1):W580-4.
23. McWilliam H, et al. (2013) Analysis Tool Web Services from the EMBL-EBI. *Nucleic Acids Res* 41(Web Server issue):W597-600.
24. Rice P, Longden I, Bleasby A (2000) EMBOSS: the European Molecular Biology Open Software Suite. *Trends Genet* 16(6):276-277.
25. Li H (2017) Minimap2: fast pairwise alignment for long nucleotide sequences. *ArXiv e-prints* 2017. Available at: https://pdfs.semanticscholar.org/a703/88011f2995783e159dc21a62905753a6af44.pdf.
26. Lindenbaum P (2015) JVarkit: java-based utilities for Bioinformatics. *figshare*. doi:10.6084/m9.figshare.1425030.v1.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

---

What is claimed is:

1. A method of nucleic acid sequencing, comprising:
producing a circularized double stranded DNA comprising a full-length cDNA, wherein the circularized double stranded DNA is produced from the full-length cDNA comprising a first heterologous sequence at its first end and a second heterologous sequence at its other end opposite the its first end, and a double stranded splint oligonucleotide comprising sequences complementary to the first heterologous sequence and the second heterologous sequence;
producing a concatemer comprising repeating segments having the sequence of the full-length cDNA and the sequence of the splint oligonucleotide by performing a rolling circle amplification using the circularized double stranded DNA as a template
obtaining a raw sequencing read of the concatemer using a nanopore sequencing device;
identifying the repeating segments in the raw sequencing read; and
producing a consensus sequence of the full-length cDNA based on the sequences of the repeating segments, wherein said identifying the repeating segments in the raw sequencing read comprises subjecting the raw sequencing read to a modified Smith-Waterman self-to-self alignment, and
wherein said subjecting the raw sequencing read to the modified Smith-Waterman self-to-self alignment comprises: identifying the sequence of the splint oligonucleotide in the raw sequencing read of the concatemer.

2. The method according to claim 1, wherein said obtaining a raw sequencing read of the concatemer using the nanopore sequencing device comprises: applying a potential difference across the nanopore of the nanopore sequencing device; and detecting electrical signals from the nanopore of the nanopore sequencing device while the concatemer is exposed to the nanopore of the nanopore sequencing device in a sequential manner.

3. The method according to claim 2, further comprising translocating at least a portion of the concatemer through the nanopore of the nanopore sequencing device.

4. The method according to claim 1, wherein said identifying the repeating segments in the raw sequencing read further comprises parsing a score matrix of the modified Smith-Waterman self-to-self alignment.

5. The method according to claim 1, wherein said producing a consensus sequence of the full-length cDNA comprises combining the sequences of the repeating segments using a partial order alignment (POA).

6. The method according to claim 1, further comprising subjecting the consensus sequence to error-correction.

7. The method according to claim 6, wherein said subjecting the consensus sequence to error-correction comprises subjecting the consensus sequence to rapid consensus module Racon.

8. The method according to claim 1, wherein said producing the circularized double stranded DNA comprises producing the full-length cDNA by performing a reverse-transcription reaction on an RNA sample of interest.

9. The method according to claim 8, wherein the full-length cDNA produced by the reverse transcription reaction is amplified prior to said producing the circularized double stranded DNA.

10. The method according to claim 9, wherein the first heterologous sequence and the second heterologous sequence are added to the full-length cDNA during the reverse transcription reaction or when the full-length cDNA is amplified.

* * * * *

SEQUENCE LISTING

```
<160> NUMBER OF SEQ ID NOS: 18

<210> SEQ ID NO 1
<211> LENGTH: 56
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: this amino acid residue contains a isocytidine

<400> SEQUENCE: 1
caagcagtgg tatcaacgca gagtactttt tttttttttt tttttttttt tttttt         56

<210> SEQ ID NO 2
<211> LENGTH: 47
<212> TYPE: DNA
<213> ORGANISM: Artificial Sequence
<220> FEATURE:
<223> OTHER INFORMATION: Synthetic sequence

<400> SEQUENCE: 2
tcgtcggcag cgtcagatgt gtataagaga cagugaauuc tggtggg                   47

<210> SEQ ID NO 3
<211> LENGTH: 47
```

```
<212> TYPE: DNA
<213> ORGANISM: Artificial Sequence
<220> FEATURE:
<223> OTHER INFORMATION: Synthetic sequence

<400> SEQUENCE: 3
tcgtcggcag cgtcagatgt gtataagaga cagacucugu tggtggg          47

<210> SEQ ID NO 4
<211> LENGTH: 47
<212> TYPE: DNA
<213> ORGANISM: Artificial Sequence
<220> FEATURE:
<223> OTHER INFORMATION: Synthetic sequence

<400> SEQUENCE: 4
tcgtcggcag cgtcagatgt gtataagaga cagcucugua tggtggg          47

<210> SEQ ID NO 5
<211> LENGTH: 47
<212> TYPE: DNA
<213> ORGANISM: Artificial Sequence
<220> FEATURE:
<223> OTHER INFORMATION: Synthetic sequence

<400> SEQUENCE: 5
tcgtcggcag cgtcagatgt gtataagaga caguaguacu tggtggg          47

<210> SEQ ID NO 6
<211> LENGTH: 47
<212> TYPE: DNA
<213> ORGANISM: Artificial Sequence
<220> FEATURE:
<223> OTHER INFORMATION: Synthetic sequence

<400> SEQUENCE: 6
tcgtcggcag cgtcagatgt gtataagaga cagggucuug tggtggg          47

<210> SEQ ID NO 7
<211> LENGTH: 47
<212> TYPE: DNA
<213> ORGANISM: Artificial Sequence
<220> FEATURE:
<223> OTHER INFORMATION: Synthetic sequence

<400> SEQUENCE: 7
tcgtcggcag cgtcagatgt gtataagaga cagauaguau tggtggg          47

<210> SEQ ID NO 8
<211> LENGTH: 47
<212> TYPE: DNA
<213> ORGANISM: Artificial Sequence
<220> FEATURE:
<223> OTHER INFORMATION: Synthetic sequence

<400> SEQUENCE: 8
tcgtcggcag cgtcagatgt gtataagaga caguccuauc tggtggg          47

<210> SEQ ID NO 9
<211> LENGTH: 47
<212> TYPE: DNA
<213> ORGANISM: Artificial Sequence
<220> FEATURE:
<223> OTHER INFORMATION: Synthetic sequence

<400> SEQUENCE: 9
```
tcgtcggcag cgtcagatgt gtataagaga cagcauucgu tggtggg                47

```
<210> SEQ ID NO 10
<211> LENGTH: 23
<212> TYPE: DNA
<213> ORGANISM: Artificial Sequence
<220> FEATURE:
<223> OTHER INFORMATION: Synthetic sequence

<400> SEQUENCE: 10
```
aagcagtggt atcaacgcag agt                                          23

```
<210> SEQ ID NO 11
<211> LENGTH: 48
<212> TYPE: DNA
<213> ORGANISM: Artificial Sequence
<220> FEATURE:
<223> OTHER INFORMATION: Synthetic sequence

<400> SEQUENCE: 11
```
aatgatacgg cgaccaccga gatctacact cgtcggcagc gtcagatg               48

```
<210> SEQ ID NO 12
<211> LENGTH: 46
<212> TYPE: DNA
<213> ORGANISM: Artificial Sequence
<220> FEATURE:
<223> OTHER INFORMATION: Synthetic sequence

<400> SEQUENCE: 12
```
actctgcgtt gataccactg cttaaaggga tattttcgat cgcttg                 46

```
<210> SEQ ID NO 13
<211> LENGTH: 47
<212> TYPE: DNA
<213> ORGANISM: Artificial Sequence
<220> FEATURE:
<223> OTHER INFORMATION: Synthetic sequence

<400> SEQUENCE: 13
```
atctcggtgg tcgccgtatc atttgaggct gatgagttcc atatttg                47

```
<210> SEQ ID NO 14
<211> LENGTH: 185
<212> TYPE: PRT
<213> ORGANISM: Artificial Sequence
<220> FEATURE:
<223> OTHER INFORMATION: Synthetic sequence

<400> SEQUENCE: 14
```

Gln Met Gly Gly Phe Tyr Leu Cys Gln Pro Gly Pro Ser Glu Lys
1               5                   10                  15

Ala Trp Gln Pro Gly Trp Thr Val Asn Val Glu Gly Ser Gly Glu Leu
            20                  25                  30

Phe Arg Trp Asn Val Ser Asp Leu Gly Gly Leu Gly Cys Gly Leu Lys
        35                  40                  45

Asn Arg Ser Ser Glu Gly Pro Ser Ser Pro Ser Gly Lys Leu Met Ser
    50                  55                  60

Pro Lys Leu Tyr Val Trp Ala Lys Asp Arg Pro Glu Ile Trp Glu Gly
65                  70                  75                  80

Glu Pro Pro Cys Leu Pro Pro Arg Asp Ser Leu Asn Gln Ser Leu Ser
                85                  90                  95

Gln Asp Leu Thr Met Ala Pro Gly Ser Thr Leu Trp Leu Ser Cys Gly

```
            100                 105                 110

Val Pro Pro Asp Ser Val Ser Arg Gly Pro Leu Ser Trp Thr His Val
            115                 120                 125

His Pro Lys Gly Pro Lys Ser Leu Leu Ser Leu Glu Leu Lys Asp Asp
    130                 135                 140

Arg Pro Ala Arg Asp Met Trp Val Met Glu Thr Gly Leu Leu Leu Pro
145                 150                 155                 160

Arg Ala Thr Ala Gln Asp Ala Gly Lys Tyr Tyr Cys His Arg Gly Asn
                165                 170                 175

Leu Thr Met Ser Phe His Leu Glu Ile
            180                 185

<210> SEQ ID NO 15
<211> LENGTH: 72
<212> TYPE: PRT
<213> ORGANISM: Artificial Sequence
<220> FEATURE:
<223> OTHER INFORMATION: Synthetic sequence

<400> SEQUENCE: 15

Gln Met Gly Gly Phe Tyr Leu Cys Gln Pro Gly Pro Ser Glu Lys
1               5                   10                  15

Ala Trp Gln Pro Gly Trp Thr Val Asn Val Glu Gly Ser Gly Glu Gly
            20                  25                  30

Arg Ala Gly Ala Gly Ala Gly Glu Lys Gly Gly His His Gly Gln
        35                  40                  45

Lys Arg Ser Ala Ala Thr Met Glu Thr Glu Leu Glu Arg Gly Ala Gly
    50                  55                  60

Gly Ile Glu Gly Glu Thr Arg Ser
65                  70

<210> SEQ ID NO 16
<211> LENGTH: 123
<212> TYPE: PRT
<213> ORGANISM: Artificial Sequence
<220> FEATURE:
<223> OTHER INFORMATION: Synthetic sequence

<400> SEQUENCE: 16

Met Ser Pro Lys Leu Tyr Val Trp Ala Lys Asp Arg Pro Glu Ile Trp
1               5                   10                  15

Glu Gly Glu Pro Pro Cys Leu Pro Pro Arg Asp Ser Leu Asn Gln Ser
            20                  25                  30

Leu Ser Gln Asp Leu Thr Met Ala Pro Gly Ser Thr Leu Trp Leu Ser
        35                  40                  45

Cys Gly Val Pro Pro Asp Ser Val Ser Arg Gly Pro Leu Ser Trp Thr
    50                  55                  60

His Val His Pro Lys Gly Pro Lys Ser Leu Leu Ser Leu Glu Leu Lys
65                  70                  75                  80

Asp Asp Arg Pro Ala Arg Asp Met Trp Val Met Glu Thr Gly Leu Leu
                85                  90                  95

Leu Pro Arg Ala Thr Ala Gln Asp Ala Gly Lys Tyr Tyr Cys His Arg
            100                 105                 110

Gly Asn Leu Thr Met Ser Phe His Leu Glu Ile
        115                 120

<210> SEQ ID NO 17
<211> LENGTH: 72
```

```
<212> TYPE: PRT
<213> ORGANISM: Artificial Sequence
<220> FEATURE:
<223> OTHER INFORMATION: Synthetic sequence

<400> SEQUENCE: 17

Gln Met Gly Gly Phe Tyr Leu Cys Gln Pro Gly Pro Ser Glu Lys
1               5                   10                  15

Ala Trp Gln Pro Gly Trp Thr Val Asn Val Glu Gly Ser Gly Glu Gly
                20                  25                  30

Arg Ala Gly Ala Gly Ala Gly Gly Glu Lys Gly Gly His His Gly Gln
                35                  40                  45

Lys Arg Ser Ala Ala Thr Met Glu Thr Glu Leu Glu Arg Gly Ala Gly
                50                  55                  60

Gly Ile Glu Gly Glu Thr Arg Ser
65                  70

<210> SEQ ID NO 18
<211> LENGTH: 35
<212> TYPE: PRT
<213> ORGANISM: Artificial Sequence
<220> FEATURE:
<223> OTHER INFORMATION: Synthetic sequence

<400> SEQUENCE: 18

Met Trp Val Met Glu Thr Gly Leu Leu Leu Pro Arg Ala Thr Ala Asp
1               5                   10                  15

Ala Gly Lys Tyr Tyr Cys His Arg Gly Asn Leu Thr Met Ser Phe His
                20                  25                  30

Leu Glu Ile
        35
```